(12) United States Patent
Mauger et al.

(10) Patent No.: US 11,517,321 B2
(45) Date of Patent: Dec. 6, 2022

(54) SYSTEM AND METHODS FOR EMBOLIZED OCCLUSION OF NEUROVASCULAR ANEURYSMS

(71) Applicant: Nanostructures, Inc., Santa Clara, CA (US)

(72) Inventors: Philip Mauger, Cupertino, CA (US); Michael Williamson, Clayton, CA (US); Mark Alan Adler, San Jose, CA (US); Justin Allen Payne, San Jose, CA (US)

(73) Assignee: Nanostructures, Inc., Santa Clara, CA (US)

(*) Notice: Subject to any disclaimer, the term of this patent is extended or adjusted under 35 U.S.C. 154(b) by 535 days.

(21) Appl. No.: 16/303,507

(22) PCT Filed: May 25, 2017

(86) PCT No.: PCT/US2017/034460
§ 371 (c)(1),
(2) Date: Nov. 20, 2018

(87) PCT Pub. No.: WO2017/205617
PCT Pub. Date: Nov. 30, 2017

(65) Prior Publication Data
US 2020/0323539 A1   Oct. 15, 2020
US 2021/0275189 A9   Sep. 9, 2021

Related U.S. Application Data

(60) Provisional application No. 62/342,135, filed on May 26, 2016.

(51) Int. Cl.
*A61B 17/12* (2006.01)
*A61B 17/00* (2006.01)

(52) U.S. Cl.
CPC .. *A61B 17/12172* (2013.01); *A61B 17/12113* (2013.01); *A61B 2017/00867* (2013.01)

(58) Field of Classification Search
CPC ........ A61B 17/12172; A61B 17/12113; A61B 2017/00867
See application file for complete search history.

(56) References Cited

U.S. PATENT DOCUMENTS 5,263,964 A   11/1993   Purdy
5,304,195 A   4/1994   Twyford et al.
(Continued)

FOREIGN PATENT DOCUMENTS

CN   102202585   9/2011
CN   105142545   12/2015
(Continued)

OTHER PUBLICATIONS

International Search Report and Written Opinion for PCT/US2017/034460 dated Aug. 28, 2017 in 16 pages.

*Primary Examiner* — Todd J Scherbel
(74) *Attorney, Agent, or Firm* — Knobbe Martens Olson & Bear, LLP

(57) ABSTRACT

The present disclosure is related to an occlusion device having a mesh structure. The occlusion device configured to transition between a two-dimensional configuration and a three-dimensional configuration. In the two-dimensional configuration and at rest, the occlusion device is flat or planar. In the three-dimensional configuration, the occlusion device defines an internal volume.

18 Claims, 25 Drawing Sheets

(56) References Cited

U.S. PATENT DOCUMENTS

| | | |
|---|---|---|
| 5,350,397 A | 9/1994 | Palermo et al. |
| 5,624,449 A | 4/1997 | Pham et al. |
| 5,749,894 A | 5/1998 | Engelson |
| 5,928,260 A | 7/1999 | Chin et al. |
| 5,980,514 A | 11/1999 | Kupiecki et al. |
| 6,036,720 A | 3/2000 | Abrams et al. |
| 6,077,291 A | 6/2000 | Das |
| 6,168,622 B1 | 1/2001 | Mazzocchi |
| 6,689,141 B2 | 2/2004 | Ferrera et al. |
| 6,746,468 B1 | 6/2004 | Sepetka et al. |
| 6,911,037 B2 | 5/2005 | Gainor et al. |
| 7,011,094 B2 | 3/2006 | Rapacki et al. |
| 8,142,456 B2 | 3/2012 | Rosqueta et al. |
| 8,444,668 B2 | 5/2013 | Jones et al. |
| 2001/0044634 A1 | 11/2001 | Don Michael et al. |
| 2002/0026211 A1 | 2/2002 | Khosravi et al. |
| 2003/0093097 A1 | 5/2003 | Avellanet et al. |
| 2003/0171739 A1 | 9/2003 | Murphy et al. |
| 2003/0187475 A1 | 10/2003 | Tsugita et al. |
| 2004/0087998 A1 | 5/2004 | Lee et al. |
| 2004/0153025 A1 | 8/2004 | Seifert et al. |
| 2004/0193206 A1 | 9/2004 | Gerberding et al. |
| 2005/0277978 A1 | 12/2005 | Greenhalgh |
| 2007/0088387 A1 | 4/2007 | Eskridge et al. |
| 2007/0191884 A1 | 8/2007 | Eskridge et al. |
| 2007/0265656 A1 | 11/2007 | Amplatz |
| 2007/0270902 A1 | 11/2007 | Slazas et al. |
| 2009/0112228 A1 | 4/2009 | Deshpande et al. |
| 2009/0112249 A1 | 4/2009 | Miles et al. |
| 2009/0112251 A1 | 4/2009 | Qian et al. |
| 2009/0112253 A1 | 4/2009 | Neilan |
| 2010/0094335 A1 | 4/2010 | Gerberding et al. |
| 2011/0319926 A1 | 12/2011 | Becking et al. |
| 2012/0065667 A1 | 3/2012 | Javois |
| 2012/0095500 A1 | 4/2012 | Heuser |
| 2012/0330341 A1 | 12/2012 | Becking et al. |
| 2013/0116722 A1* | 5/2013 | Aboytes ........... A61B 17/12172 606/198 |
| 2013/0325053 A1 | 12/2013 | Porter |
| 2014/0288633 A1 | 9/2014 | Burke et al. |
| 2015/0216534 A1 | 8/2015 | Riina et al. |
| 2015/0272590 A1 | 10/2015 | Aboytes et al. |
| 2015/0297240 A1* | 10/2015 | Divino ............. A61B 17/12168 606/200 |
| 2015/0374483 A1* | 12/2015 | Janardhan ............... A61M 1/74 606/200 |
| 2016/0022275 A1 | 1/2016 | Garza |
| 2016/0022445 A1 | 1/2016 | Ruvalcaba et al. |
| 2016/0051263 A1 | 2/2016 | Morsi |
| 2016/0120551 A1 | 5/2016 | Connor |
| 2016/0166257 A1 | 6/2016 | Wayne et al. |
| 2016/0220265 A1 | 8/2016 | Pokomey |
| 2016/0324668 A1 | 11/2016 | Wallace et al. |
| 2016/0374690 A9 | 12/2016 | Connor |
| 2017/0027552 A1 | 2/2017 | Turkington et al. |
| 2017/0128077 A1 | 5/2017 | Hewitt et al. |
| 2017/0143359 A1 | 5/2017 | Nguyen et al. |
| 2017/0156734 A1 | 6/2017 | Griffin |
| 2017/0165046 A1 | 6/2017 | Johnson et al. |
| 2017/0189035 A1* | 7/2017 | Porter ............... A61B 17/12031 |
| 2017/0367710 A1 | 12/2017 | Yang |
| 2017/0367713 A1 | 12/2017 | Greene et al. |
| 2018/0098777 A1 | 4/2018 | Gabbay |
| 2018/0103971 A1 | 4/2018 | Imai et al. |
| 2018/0147041 A1 | 5/2018 | Chouinard et al. |
| 2018/0153674 A1 | 6/2018 | Walzman |
| 2018/0206850 A1 | 7/2018 | Wang |
| 2018/0296224 A1 | 10/2018 | Kealey et al. |
| 2018/0311029 A1 | 11/2018 | Hocking et al. |
| 2019/0046343 A1 | 2/2019 | Choubey |
| 2019/0142435 A1 | 5/2019 | DeMeritt |
| 2019/0223876 A1 | 7/2019 | Badruddin et al. |
| 2019/0343664 A1 | 11/2019 | Ruvalcaba et al. |
| 2021/0052278 A1 | 2/2021 | Mauger et al. |

FOREIGN PATENT DOCUMENTS

| | | |
|---|---|---|
| CN | 105142546 | 12/2015 |
| CN | 105007859 | 7/2018 |
| CN | 111936063 | 11/2020 |
| EP | 2932921 | 10/2015 |
| EP | 3745965 | 12/2020 |
| JP | 2017-516605 | 6/2017 |
| WO | WO 2010/028314 | 3/2010 |
| WO | WO 2013/103888 | 7/2013 |
| WO | WO 2013/142756 | 9/2013 |
| WO | WO 2014/144980 | 9/2014 |
| WO | WO 2016/137997 | 9/2016 |
| WO | WO 2017/106567 | 6/2017 |
| WO | WO 2017/205617 | 11/2017 |
| WO | WO 2019/152434 | 8/2019 |

* cited by examiner

SYSTEM AND METHODS FOR EMBOLIZED OCCLUSION OF NEUROVASCULAR ANEURYSMS

CROSS-REFERENCE TO RELATED APPLICATIONS

The present application is a U.S. National Phase of International Application No. PCT/US2017/034460, filed May 25, 2017, which claims priority benefit under 35 U.S.C. § 119(e) to U.S. Provisional Patent Application Ser. No. 62/342,135, filed May 26, 2016, titled SYSTEM AND METHODS FOR EMBOLIZED OCCLUSION OF NEUROVASCULAR ANEURYSMS, all of which applications are hereby incorporated by reference in their entirety.

BACKGROUND

Field

This application is related to methods and devices for treating neurovascular aneurysms.

Description of the Related Art

The worldwide occurrence of stroke is estimated to be in the vicinity of 60,000,000 instances per year. The economic and social costs for strokes are enormous. While most strokes are fatal or debilitating, even mild strokes often result in impairment that greatly diminishes quality of life and independence while substantially increasing direct costs for healthcare and daily living. Further, indirect costs such as lost productivity, expanded burden on care provided by immediate family, and the allocation of limited resources to rehabilitative therapy and convalescence aggregate to create a significant unmet need for the prevention of stroke beyond the current standard of care.

While advances in medical science, standards of care, preventative actions, and an understanding of the influences of personal lifestyle have improved in the field of stroke over time, the causes of stroke are complex and not fully understood in all instances. Stroke is divided into two categories: ischemic (loss of normal blood flow) and hemorrhagic (bleeding through blood vessel rupture).

A brain (cerebral) aneurysm is a bulging, weak area in the wall of an artery that supplies blood to the brain. If a brain aneurysm ruptures (a subarachnoid hemorrhage), it releases blood into the skull resulting in stroke. Depending on the severity of the hemorrhage, brain damage or death may result.

The risk factors for formation of aneurysms are recognized to include genetics, gender, age, race, elevated blood pressure, smoking, and atherosclerosis. In many cases an unruptured cerebral aneurysm may only be discovered during tests for another, usually unrelated, condition. In other cases, an unruptured cerebral aneurysm will cause problems by pressing on areas in the brain. When this happens, the person may suffer from severe headaches, blurred vision, changes in speech, and neck pain, depending on what areas of the brain are affected and how severe the aneurysm is.

SUMMARY

At present there are three treatment options for people with the diagnosis of cerebral aneurysm: (1) medical (non-surgical) therapy; (2) surgical therapy or clipping; and (3) endovascular therapy or coiling.

Medical therapy is usually only an option for the treatment of unruptured intracranial aneurysms. Strategies include smoking cessation and blood pressure control. These are the only factors that have been shown to have a significant effect on aneurysm formation, growth, and rupture. Periodic radiographic imaging may be used to monitor the size and growth of an aneurysm. However, because the mechanisms of aneurysm rupture are not entirely understood, and because even aneurysms of very small size may rupture, monitoring cerebral aneurysms is an incomplete solution to meeting medical needs.

Surgical treatment of cerebral aneurysms has existed for more than 150 years, and for more than 80 years the standard of care has included the use of aneurysm clips which have evolved into hundreds of varieties, shapes, and sizes. The mechanical sophistication of available clips, along with the advent of the operating microscope in the 1960s have made surgical clipping the gold standard in the treatment of both ruptured and unruptured cerebral aneurysms.

Surgical clipping remains an invasive and technically challenging procedure whereby the brain and the blood vessels are accessed through an opening in the skull. After the aneurysm is identified, it is carefully separated from the surrounding brain tissue. A small metal clip is secured to the base of the aneurysm. The choice of a particular clip configuration is based on the size and location of an aneurysm. The clip has a spring mechanism which allows the clip to close around either side of the aneurysm, thus occluding the aneurysm from the blood vessel. Normal blood vessel anatomy is physically restored by excluding the aneurysm sac from the cerebral circulation.

Endovascular techniques for treating aneurysms date back to the 1970s with the introduction of proximal balloon occlusion. Guido Guglielmi an American-based neuroradiologist, invented the platinum detachable microcoil, which was used to treat the first human being in 1991.

Endovascularly delivered coils are soft wire spirals originally made out of platinum. These coils are deployed into an aneurysm via a microcatheter that is inserted through the femoral artery of the leg and carefully advanced into the brain. The microcatheter is advanced into the aneurysm itself, and the microcoils are released in a sequential manner. Once the coils are released into the aneurysm, the blood flow pattern within the aneurysm is significantly reduced, leading to thrombosis (clotting) of the aneurysm. A thrombosed aneurysm resists the entry of liquid blood, providing a seal in a manner similar to a clip.

Endovascular coiling is an attractive option for treating aneurysms because it does not require opening of the skull, and is generally accomplished in a shorter timeframe, which lessens the impact of physical strain on the patient. A limitation of coiling is that eventual compression of the bolus of individual coils may compress over time and thus blood flow to the aneurysm may become reestablished. Additionally, not all aneurysms are suitable for coiling: (1) wide-necked aneurysms require a support scaffolding (usually a stent) as a structural support to prevent prolapse of the coil bolus into the blood vessel; (2) aneurysms that are located in the distal reaches of the neurovasculature may lie beyond the reach of current microcatheter sizing; and, (3) microcatheters filled with embolic coils are not always flexible enough to navigate the highly tortuous and fragile anatomy of neurovascular blood vessels. As experience with coiling grows, the indications and pitfalls continue to be refined. Endovascular and coil technology continue to improve: endovascular adjuncts, such as intracranial stents, are now available to assist in coiling procedures; the original platinum microcoil has been refined with ever-improving features such as biological coating and microengineering for efficiency in deployment.

More recently, endovascular devices alternative to coils have begun to open further options for the treatment of aneurysms. Blood flow diversion without coils may provide a less expensive, more efficient, and more adaptive means for the treatment of aneurysms. Nickel-titanium-based (NiTi) flow diversion structures provide further options for physicians and patients. At present, laser cut hypotube or braided wire form the structures from which flow diverters are made. Laser cut hypotubes require complex manufacturing and have limitations in the degree of expansion deformation that they can tolerate. Alternately, braided wire forms are much less complicated to manufacture, can tolerate substantial expansion deformation, but offer very limited control of structural porosity due to the localized unconstrained movement allowable between wires that are not mechanically bound together.

Therefore, a substantial need exists to increase minimally invasive and cost-effective solutions to improve intracranial access using systems and methods to control the risk and effects of hemorrhagic stroke through means of very small, highly capable, and reliably producible interventional tools and implants.

Some aspects of the present disclosure provide the means and the methods for treating cerebral aneurysms via a catheter-based, minimally invasive interventional system that includes a blood flow diverting implant that is placed within the aneurysm sac.

Some aspects of the present disclosure include deploying the implant from a microcatheter having an outer diameter of 0.027 inches or less, for example 0.021 inches or less at the distal working area of the microcatheter. Manufactured with polymer, metal and polymer, polymer and thin film, polymer and integrated braided material for torque control, and integrated tether mechanism or tether line for release of the implant. The release may be completed by mechanical energy, or absorbed or by delivered energy such as thermal or electrical or by environmental energy from thermal body temperature transfer.

Some aspects of the present disclosure provide a restraint for restraining, and optionally recapturing, an implant so as to aid in the accurate positioning and deployment of an implant in situ.

Some aspects of the present disclosure are directed toward an implant for treating an aneurysm that is a blood flow diverter (e.g., occluder) comprised of thin-film NiTi. When deployed, the NiTi implant may be in the martensitic (shape memory) state, the austenitic (superelastic) state, or a mixture of both or may be a multilayer of several film compositions. For example, a deployed NiTi implant is more austenitic than martensitic in situ.

Some aspects of the present disclosure are directed toward an implant for treating an aneurysm that is a blood flow diverter (e.g., occluder) comprised of an acceptable biocompatible metal including, but not limited to, biocompatible stainless steel, tantalum, tungsten, titanium, TiNi, platinum, or combinations or multilayers thereof. The metal shall be of a medical biocompatible material that may be delivered into the aneurysm utilizing balloon, wire or assisted delivery by other means, or encapsulated and then released.

In some configurations, the self-expanding implant may include NiTi thin-film, wherein the film is initially formed in a substantially flat or planar, two-dimensional form and then subsequently shaped into a three-dimensional form prior to incorporation into a catheter. In three-dimensional form, the implant may be a sphere or other enclosed or semi enclosed structure made of a hollow, semi hollow, or fully-filled thin film body. The surface area may be many times greater than volume when conformed for delivery to the specific site of treatment.

The thin film NiTi implant may be combined with additional wire, foil, and/or thin film elements either before or after shaping to provide added structural elements. The NiTi material would shape within the range of body temperature from as low as a set temperature 34 degrees centigrade and as high as 40 degrees centigrade.

In some configurations, the deployed implant may include a portion that conforms to the opening at the neck of an aneurysm.

In some configurations, the deployed implant may include a bottom portion that diverts blood flow away from the neck and sac of an aneurysm and is comprised to include one or more additional portions that fill at least some of the sac of an aneurysm.

In some configurations, the implant may include NiTi thin film, wherein the film is initially formed in a partially three-dimensional form and then subsequently further shaped into a final three-dimensional form prior to incorporation into a catheter.

In some configurations, the implant may include NiTi thin film, wherein the film is initially formed at least partially or at least substantially in three-dimensional form prior to incorporation into a catheter.

Some aspects of the disclosure are related to implants including NiTi thin film, wherein the film may be comprised of a regularly repeating pattern of meshed structures (e.g., regularly repeating porosity), wherein the meshed structures may be any pattern that optimizes the film's ability to expand from a highly compressed state that can loaded into a catheter to a substantially expanded state after release into the aneurysm while also optimizing the degree of localized stress and strain experienced by elements of the mesh.

Some aspects of the disclosure are related to implants including NiTi thin film, wherein the initial flat or planar form of the device may be shaped such that it can be formed into a three-dimensional shape as desired for deployment into an aneurysm prior to incorporation into a catheter and then unfolded into a different three dimensional shape conducive to loading into a catheter, such that upon deployment from the catheter the device returns to the first shape.

Some aspects of the disclosure are related to implants including NiTi thin film, wherein the film may be comprised of a regularly repeating pattern of meshed or perforated structures, wherein the structures may be any pattern porosity that optimizes the occlusive performance of the structure.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Figure 1:
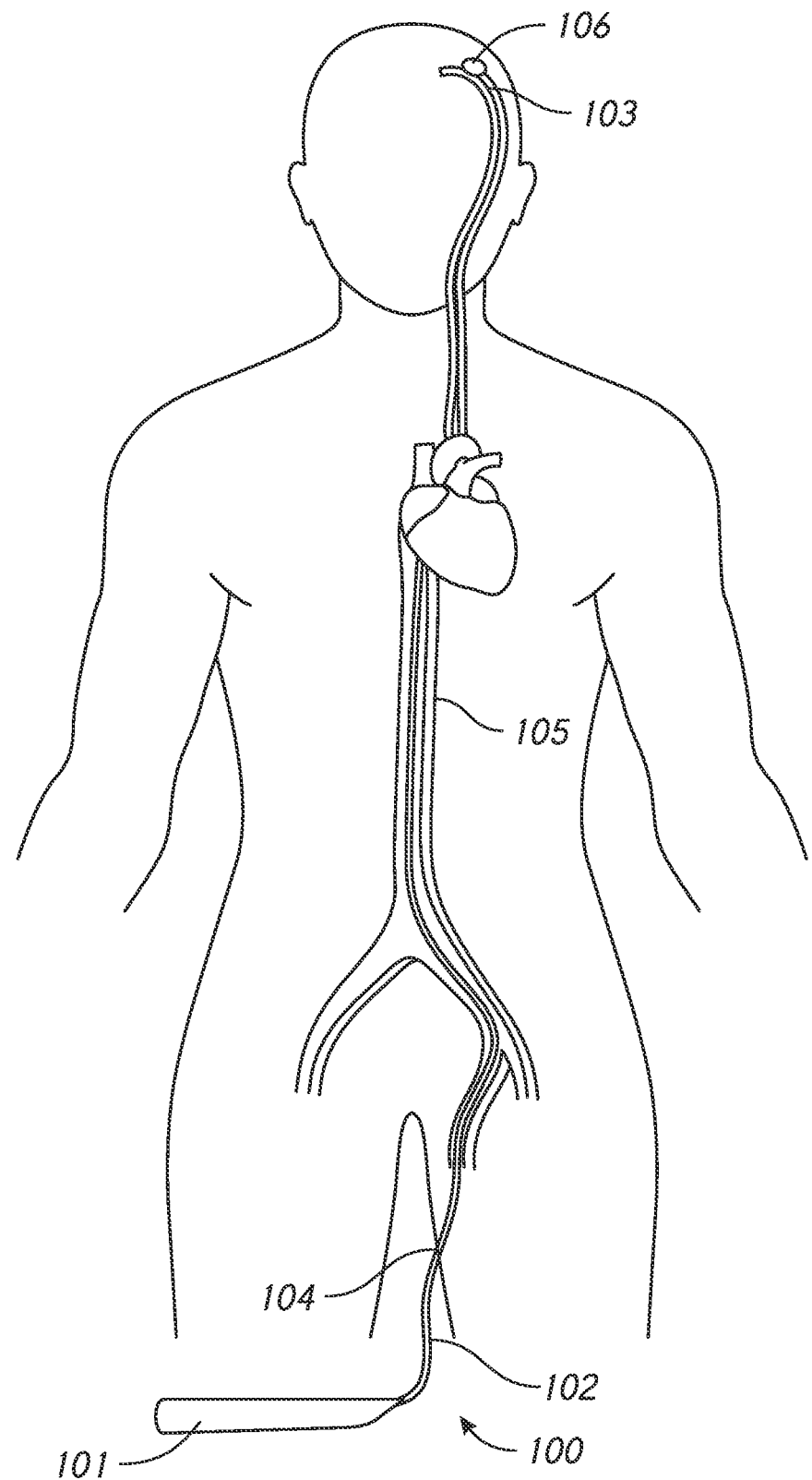
FIG. 1 shows a schematic view of the interventional system of the present disclosure in a representative access pathway to a cerebral aneurysm.

As has been previously explained herein, there remains a need for further advancement in minimally invasive interventional treatment of cerebral aneurysms. The tortuous anatomy, small vessel diameter, and uniquely delicate anatomy of the neurovasculature provides for a particularly challenging set of constraints in which an interventional system must operate. There is little room for error given that even the smallest unintended consequences of an error often result in significant negative consequences for a patient.
Delivering the Implant When treating a cerebral aneurysm, a system should be able to navigate the access pathway to the target site. As is shown in FIG. 1, a typical method is to access a femoral blood vessel at location 104 and traverse access pathway 105 through the heart and into the cranial cavity to an aneurysm location 106 that is substantially distal from access location 104. This is done with known interventional techniques which may include system 100 of the present disclosure comprised of a complex set of features which may be subdivided into principal functional subsystems comprised of control handle 101, catheter body 102, and catheter distal working end 103 (further containing an implant).

System 100 should possess enough rigidity to traverse the torso and its circulatory system along pathway 105, and then the more distal, tortuous, delicate and small diameter vessels of the cranium until target aneurism location 106 is reached. System 100 should be able to track to location 106 along pathway 105 through a micro guide catheter, over a guide wire, or on its own via natural shaping of catheter body 102 and/or steerable control from the proximal end via control handle 101.

Access to more distally located targets becomes limited by the size and stiffness of catheter working end 103, which in turn may be limited by the physical aspects of the implant contained therein. A solution to this problem of limitation is to provide an implant structure that provides the simultaneous abilities of compressing to a very small diameter, below 0.021 inches, e.g., smaller than 0.019 inches, while remaining flexible in its compressed state, and then being able to expand to many times its compressed diameter in order to fixate and perform safely in situ.

Tracking, manipulation, sheath control, compatibility with guidewires and other access tools and techniques are incorporated into the assembly and use of catheter system 100. The implant loaded into working end 103 may be radially compressed and/or folded similar to the way that angioplasty balloons and stents are loaded to reduce the profile of the distal section of a polymer delivery system, where a guide wire lumen and an outer lumen and a working end 103 where the implant is covered with a sheath. The sheath may be retracted releasing the implant to target site 106 or the implant may be pushed or manipulated from control handle 101 at the proximal end of catheter system 100 using a mandrel, guide wire or braided shaft, or other such means providing pushable force transmission a columnar strength through tortuous anatomy such that the load bearing unit is able to effect the desired action at working end 103 to deliver an implant to target site 106.

Additionally, catheter system 100 may also integrate a tethered line connected to the implant at working end 103 and extending proximally through catheter body 102 to control handle 101 which enabling catheter system 100 system to recapture or reposition the implant prior to completing deployment at target site 106.

One example of tethering means may include a tether comprised of a lubricious polymer tied by a slip knot method where one end of the line is integrated with the catheter body 102 and the second end is able to be controlled an communicated with by the user at control handle 101.

Another example of tethering means may include dissoluble material that interacts with blood or fluids and breaks down over the standard duration of the implant procedure such that the implant is released when the tether line is broken by erosion, the application of force, or both.

Figure 10A:
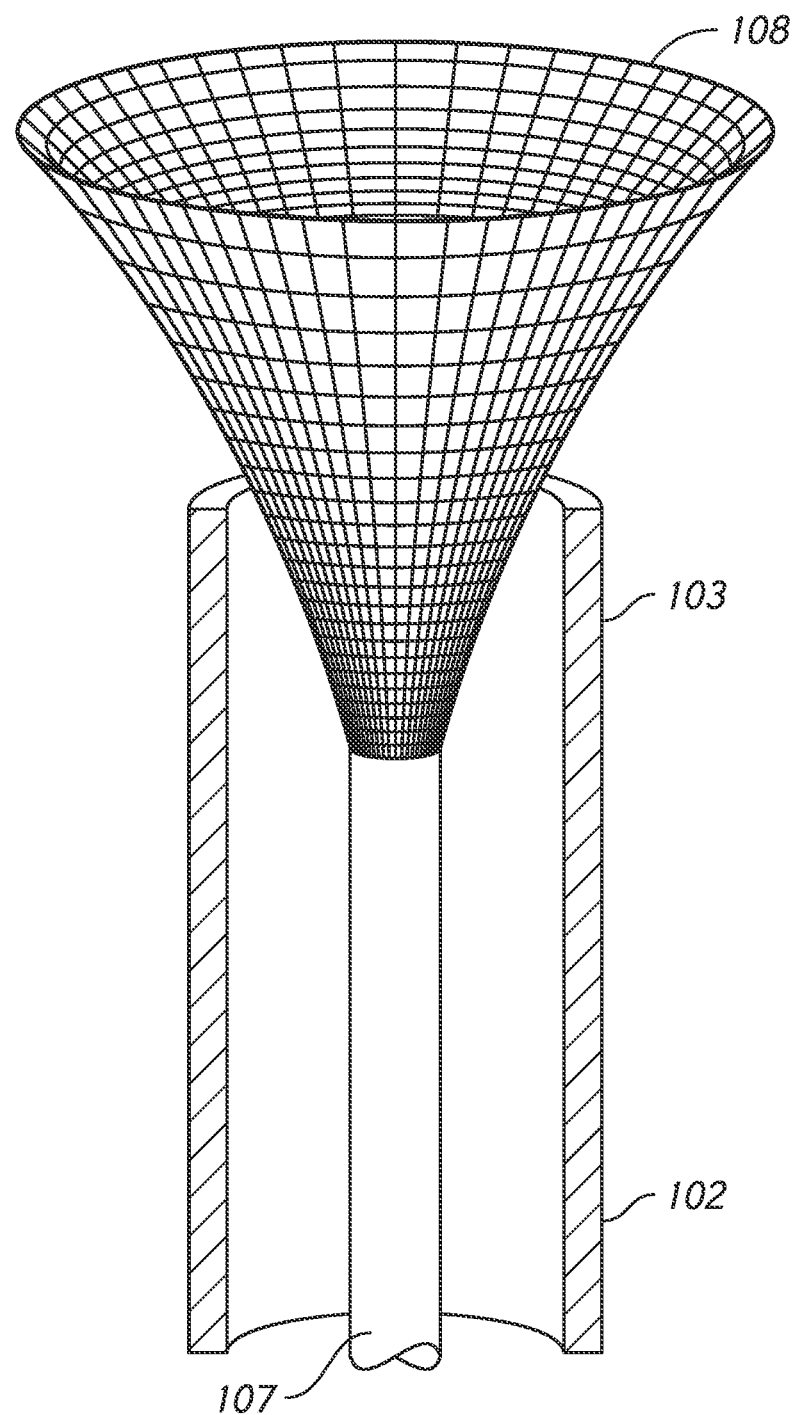
FIG. 10A shows a schematic depiction of an exemplary embodiment of a restraint at the working end of the system shown in FIG. 1.
Figure 10B:
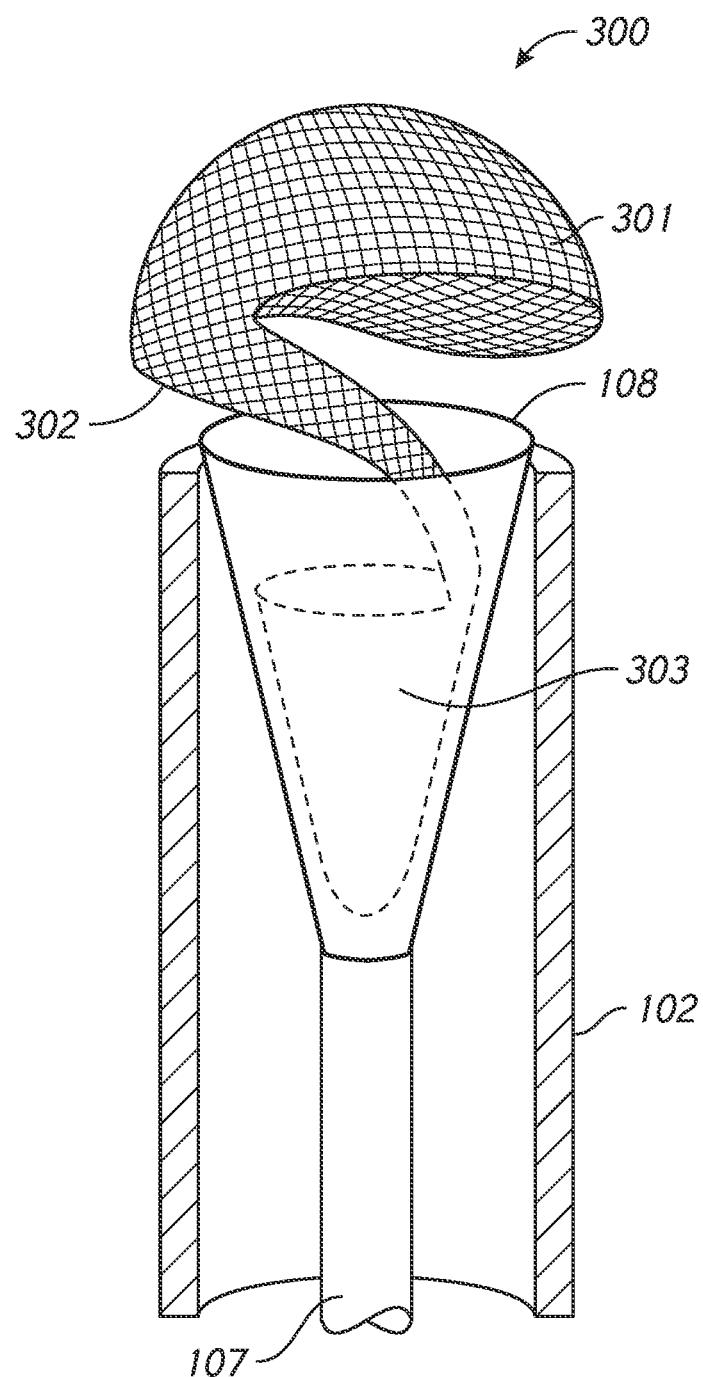
FIG. 10B shows a schematic depiction of the restraint of FIG. 10A in use deploying the implant of FIGS. 3A-3D.

Additionally referring to FIGS. 10A-10B, yet another example of a tether or restraint may be comprised of a mesh thin film or braided material 108 connected to a delivery wire 107 inside of catheter body 102 at working end 103, wherein delivery wire 107 and restraint 108 may be joined using any means of attachment known in the art, such as: energy-based fusion (such as heat); chemical bonds and adhesives; mechanical means such as crimping, interference fits, swaging, press fitting; and the like. A suitable connection joint should be able to withstand tensile loads equal to or greater than 0.1 Newtons.

Restraint 108 may further double as a snare which may be configured as a cone (as shown by example 108), a collet, a leaflet of 3 sides, or other such structures that expand and collapse with minimal outward force but shall open when released and/or not bound by the constraint of working end 103. The material of restraint 108 in such application may be of any medical-grade engineering material such as metals, polymers, textiles and the like, for example NiTi and further optionally being at least partially in the austenitic phase.

As is illustrated by FIG. 10B, restraint 108 may be compressed into the inside diameter of working end 103 of catheter body 102 of delivery system 100 while maintaining a sufficient grip on implant 300 stored and deployed from the inner diameter of working end 103. As is shown, upper portion 301 and middle portion 302 are in mid-deployment while the majority of restraint 108 and lower portion 303 of implant 300 remain constrained inside catheter body 102 until delivery wire 107 is advanced distally to further expose them. Optionally, an implant may be comprised to include a structure to mechanical interface with restraint 108 through structures such as: a formed nipple; a shaped eyelet; a nodule shape; round or non-round protrusions or recesses. While restraint 108 and implant 300 are constrained by working end 103, both are in a state of mechanical interaction that allows the implant to not be fully released and deployed to target location 106. The ability to recapture, reposition, or otherwise positionally manipulate an implant prior to being fully deployed from working end 103 to target site 106 is particularly advantageous for vascular interventional procedures where the accuracy of a permanent implant is of critical importance and the physician is limited by the tools that may be used in such minimally invasive methods. When doubling as a snare, restraint 108 should provide sufficient retention force on the implant at working end 103 so as to provide the structural strength to allow for recapture of an implant until it is released, with up to as much as two-thirds of the implant being exposed from working end 103 while maintaining recapturability.

The implant may also be non-tethered and placed at the end of a push rod and affixed thereto via a chemical bond, such as a layer of polymer bonded by heat or chemical, allowing for sufficient attachment force during the delivery and deployment procedure but is releasable upon erosion, the application of force, or both.

The delivery system may have an attached mesh, cage, or sheath like material made from thin film NiTi, braided metallic wire of biocompatible material or braided polymer and connecting to an inner shaft and the ID of the outer shaft which when both are manipulated the interaction in two directions cause the release of the implant from its constrained state into the selected site of delivery.

The outer shaft may also be maintained stationary in the selected position and only the inner shaft is moved to release the implant from its constrained position. The outer and inner shaft may also be held static in selected positions and a third shaft of smaller configuration than the inner ID be used as a pusher shaft to release the thin film from its constrained condition. The outer and inner shaft may also be static in selected positions and the temperature change enables the thin film to free itself from its constrained position and spring forward into the delivery site.

All of these possible configurations shall be compatible with other common methods of treatment to ensure the product is able to be used without limitation. Such treatments include gamma radiation, EO sterilization, and E-Beam. These shall not hinder but may complement the complete device in its function to deliver the implant from its constrained configuration.

Loading the implant into the delivery system may be done to enable the compete loaded device to be sterilized as a fully assembled item or the sterilized implant may be provided in a loading device—similar to a syringe (but with a augmented cannula) where the sterilized NiTi implant is loaded into the delivery system distal end at the time of use thus enabling delivery to the desired treatment site within the body by the delivery system.

The occluder may be retained in an outer lumen or double lumen with the delivery system push rod in tracking to the delivery site and then the push rod shall be moved in reference to the lumen for release.

Methods of Delivering an Implant

The occluder shall be able to loaded into a delivery system that shall be of specific length based on the vascular system access location to reach the location of the aneurysm or area of disrupted blood flow created by a primary artery with a non-uniform wall (a disproportionate wall caused by disfiguration of the artery) while still maintaining the blood flow. The Thin Film implant device is compressed to comply with the inner diameter of the delivery system and may be carried on a rigid, semi-rigid, or completely flexible spine system made from different implantable materials or similar or equivalent implantable material able to contain and release the device, as depicted in FIGS. 5C, 5D, 5E and 10A.

At this location, placement of an occluder in the primary artery/capillary to fill the disproportionate wall volume and enabling the human body natural endothelization, or clotting, to clot and seal off the disproportional wall section from the primary vessel.

The retention of the occluder in the delivery system shall be achieved by an interference fit to the inner push rod and the extended area created by a shape material which can be integrated to the inner delivery push rod and with the occluder mated with the delivery push rod such that when finished crimping the distal end of the delivery system push rod shall maintain a retention, measurable by the tension force to pull the occluder from the delivery system push rod and when the delivery push rod end, retaining the occluder, achieves desired and material set temperature, the delivery retention shall open allowing the release of the occlude. The delivery may be an action of 2 opposing motions, with dual action vectors, to release the implant from its cradling mechanism in the delivery system or a simple single action, mono directional vector.

Implant

Any of the implants described below can be used with the delivery systems and methods described above.

Figure 2A:
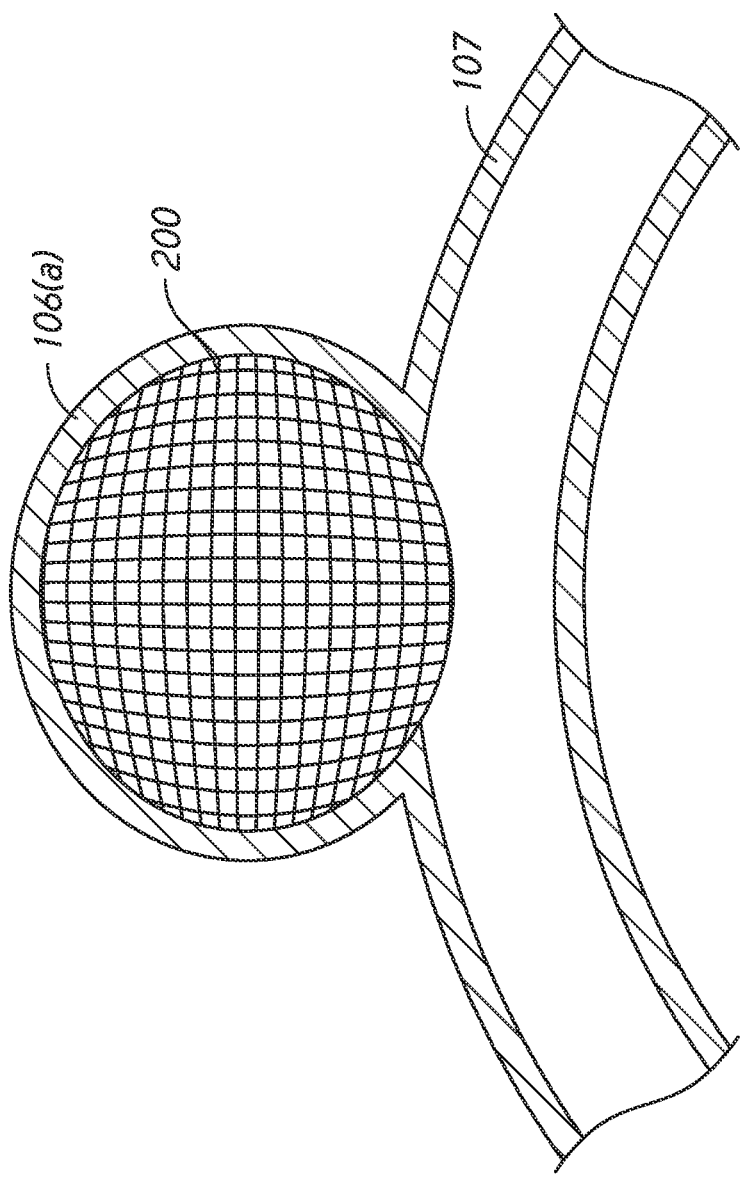
FIG. 2A shows a representative example of an aneurysm, located laterally along the length of a blood vessel, with a representative example of an implant located therein.
Figure 2B:
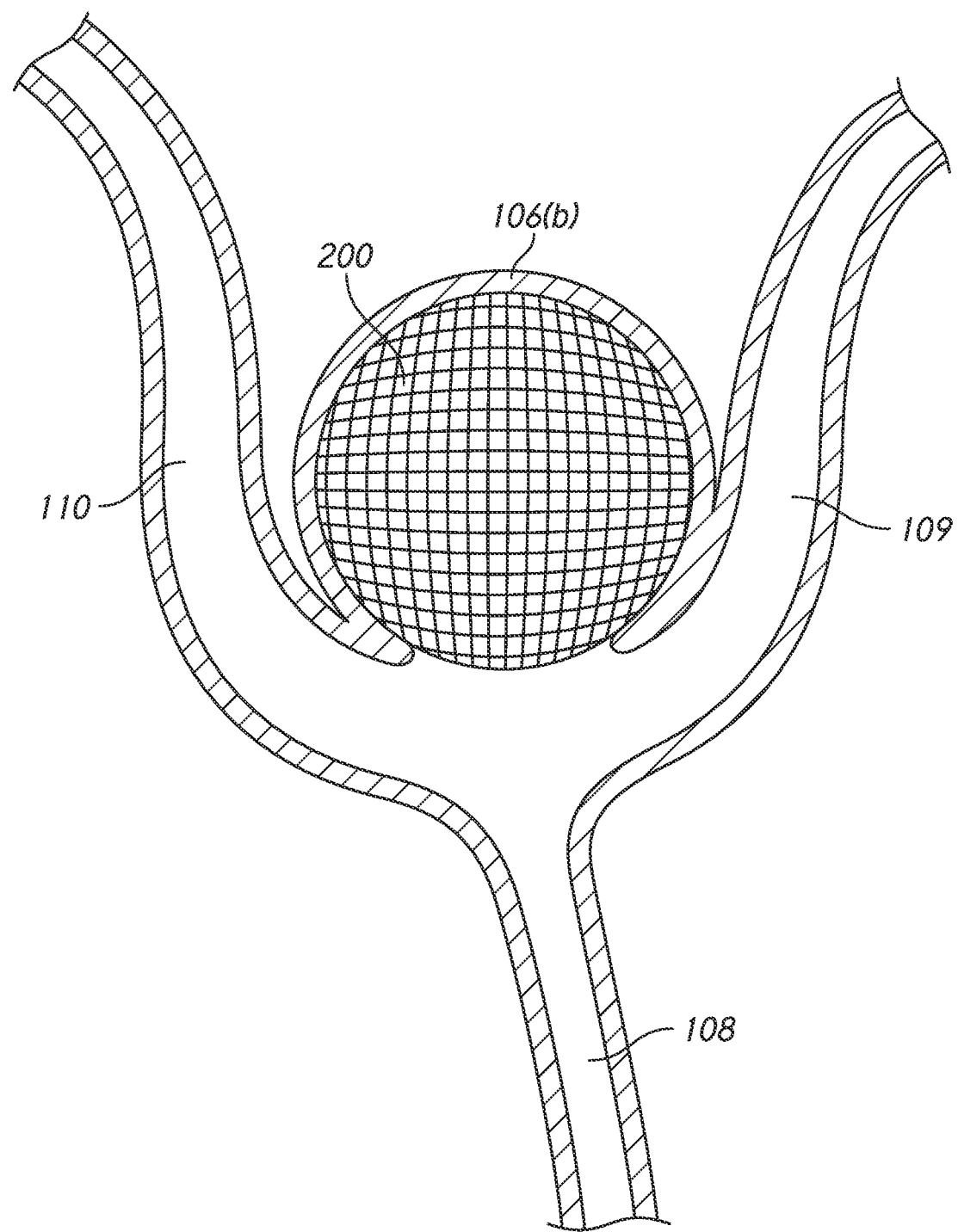
FIG. 2B shows a representative example of an aneurysm, located at the bifurcation of a blood vessel, with a representative example of an implant located therein.

Referring now to FIGS. 2A and 2B, cerebral aneurysms come in differing types. Two representative examples are the aneurysm 106(a) formed laterally along the side of neurovascular vessel 107, and the aneurysm 106(b) formed at the bifurcation of neurovascular vessel 108 into branch vessels 109 and 110. In either case, an implant 200 representative of at least one aspect of the present disclosure is shown in situ in its deployed and fixed state. Any of the features described with respect to these representative implants can apply to any of the embodiments described below.

Blood flow diversion is an aspect of implant 200, which does not require an absolutely solid surface in order to be effective. The ideal result is to provide a structure that is supple enough to avoid placing harmful pressure on the inner wall of the aneurysm sac 106(a) or 106(b), while occluding blood flow within the sac, and while diverting blood flow back into the healthy normal pathways of the native vessel(s), and while having enough mechanical strength to safely fix in place.

A fine mesh is well suited to such requirements, where the porosity of the mesh (e.g., open area of each pore) may range from about, 50 microns to about 1500 microns, and most ideally about 100 microns to about 1000 microns. Each of the implants described herein can include a mesh structure for blood flow diversion is that the mesh be of a substantially uniform porosity in the two-dimensional configuration and the three-dimensional configuration. When transformed from a two-dimensional configuration to a three-dimensional configuration, the pore size or open area of each pore in the three-dimensional configuration changes less than 20% (or less than 15%, or less than 10%, or less than 5%) than the pore size or open area of the same pore in the two-dimensional configuration. In each of the two-dimensional configuration and the three-dimensional configuration, there is less than 20% (or less than 15% or less than 10% or less than 5%) variation between the pore size or open area of any two openings. In each of the two-dimensional configuration and the three-dimensional configuration, there is less than 20% (or less than 15% or less than 10% or less than 5%) variation between the pore size of any opening and the mean pore size of the entire porosity. In some configurations, every pore and opening has a uniform size in the two-dimensional configuration and/or three-dimensional configuration.

Currently, meshes of this nature are constructed from braided NiTi wire. However, a braided structure inherently allows the individual wires of the braid to move past one another such that the unit cells formed by individual braided strands are inconsistent (uncontrolled) in size due to deformations that naturally occur during shaping and/or handling prior to deployment. Additionally, as layers of wire stack up in a compressed and catheterized braided implant, stiffness develops that may lead to limitations in distal vascular access and/or further localized deformations of an implant's braided unit cells.

These problems may be improved by creating a mesh structure from a monolithic material which may include any medical grade material (metal, polymer, etc.) that is suitable for meeting the competing criteria previously described. One particular material is NiTi which has been formed in a film-like thickness and patterned to have a mesh structure therein. The thin film may further be created by using film deposition and patterning processes. Moreover, intraluminal devices such as stents require aggressive antiplatelet therapy and are associated with higher thromboembolic (TE) complication rates. Intravascular flow disrupters (IFD) are currently braided-wire devices designed to achieve flow disruption at the aneurysm neck without placing material in the parent vessel and without the need of antiplatelet therapy. In addition to the limitations of braided wire structures previously described herein, better system performance may be achieved by producing IFDs made from NiTi thin films. As opposed to a braided structure, a thin film structure may be patterned such that the mesh is either symmetrically repetitive or otherwise preferentially patterned in an asymmetric way so as to account for surface performance optimization for a three dimensional shape based on the portion against the wall of the aneurysm sac and the portion in contact with, and diverting, blood flow. One or more of these thin film features can be applied to any of the implant embodiments described herein.

The implants described herein can transform from a first, substantially flat or planar configuration to a second, three-dimensional configuration having an internal volume. The implant can be formed from a continuous or monolithic sheet (e.g., thin film layer). The continuous or monolithic sheet can have a substantially uniform thickness. The thickness can be less than or equal to 0.005 inches, less than or equal to 0.003 inches, less than or equal to 0.002 inches, or less than or equal to 0.001 inches.

The implant can be patterned with a structural mesh that maintains substantially uniform porosity. The implant can be shape set to achieve the designated configuration (e.g., spherical, partially spherical, elliptical, etc.) with a major and minor diameter, or a three-axis diameter with equal diameters, or two equal diameters and one unequal, or two unequal diameters, or all unequal diameters, that when released into the treatment site shall optimally fill the aneurysm and fill, block, or shield the neck transition (primary artery to aneurysm void from the same vessel wall) to the aneurysm space. In the three-dimensional configuration, the implant has sufficient structural support to maintain its shape in a fluid pressure environment equivalent or greater to the level of high blood pressure (e.g., 3/2 psig; similar to diastolic/systolic in mm of HG for high blood pressure).

The substantially flat or planar configuration can include rounded, circular, elliptical, cone, and other polygonal segments. Three dimensional configurations may comprise all the facets of the 2 dimensional configurations with the introductions of additional axes at defined points as determined by how the film is manipulated prior to shape setting to create a three dimensional structure.

The implants described herein can be compressed into a small configuration by crimping in a circle or folding as a two fold, three fold, four fold and/or more folds, similar to angioplasty balloon folding, without significantly work hardening the material to change its desired properties for filling and acting as the neuro-aneurysm filler.

Figure 3A:
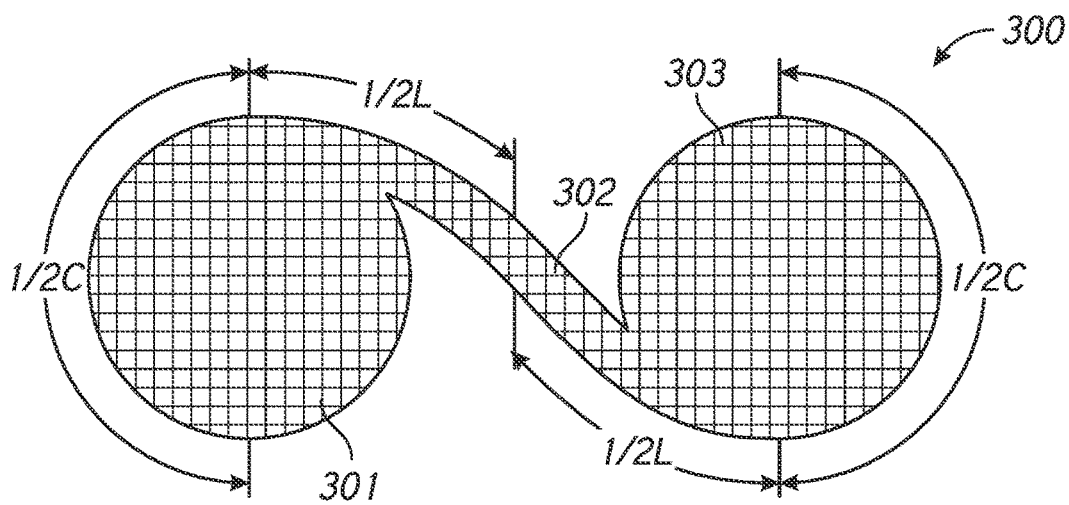
FIGS. 3A-3E show a schematic depiction of an implant embodiment during its forming process.
Figure 3B:
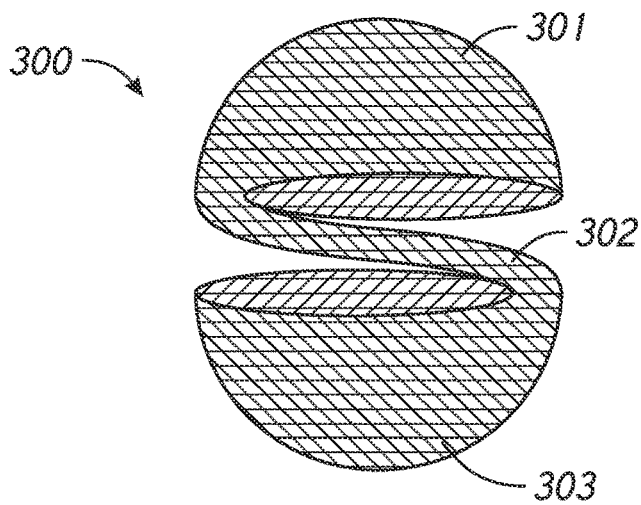
Figure 3C:
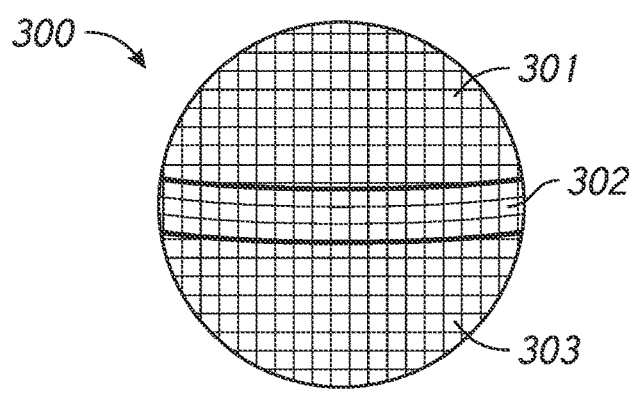

Referring now to FIGS. 3A-3C, an example of a thin film NiTi mesh structure 300 is shown. FIG. 3A shows a deposited and patterned sheet of thin film NiTi in a substantially flat or planar state. An upper segment 301 and a lower segment 303 are joined by connecting segment 302. Segments 301 and 303 may be symmetrical to one another or asymmetrical. The representative example in FIGS. 3A-3C is symmetrical but will be appreciated as including the dimensional variations that would accommodate asymmetry. In the example, implant 300 is comprised of a mesh having the segments described. Segments 301 and 303 are circular, having a circumference of "C", and are connected by element 302 having a length "L" which is equal to C when measured at the points of outer surface tangency between elements 301, 303, and 302.

As the substantially flat or planar configuration of FIG. 3A is shaped into the three dimensional shape shown in FIGS. 3B and 3C, it can be seen how a planar structure evolves through shaping. Shaping may be achieved through the combination of mechanical deformation and heat treatment. Very often, successive incremental steps are required to transform the structure from its initial to its final shape. The forming steps and heat treatment process are a function of the strains involved in forming and the desired final mechanical properties of the three dimensional structure. In this example, structure 300, when in its compressed state, forms the spheroid shape of FIG. 3C while continuing to possess flexibility (e.g., some degrees of freedom offered by the segmented design), as illustrated in a not-fully-compressed state shown in FIG. 3B. While a spheroid shape is used for example purposes, other three dimensional shapes, such as partially spherical shapes, and segment combinations may be used to achieve the concept of this aspect of the present disclosure.

Figure 12A:
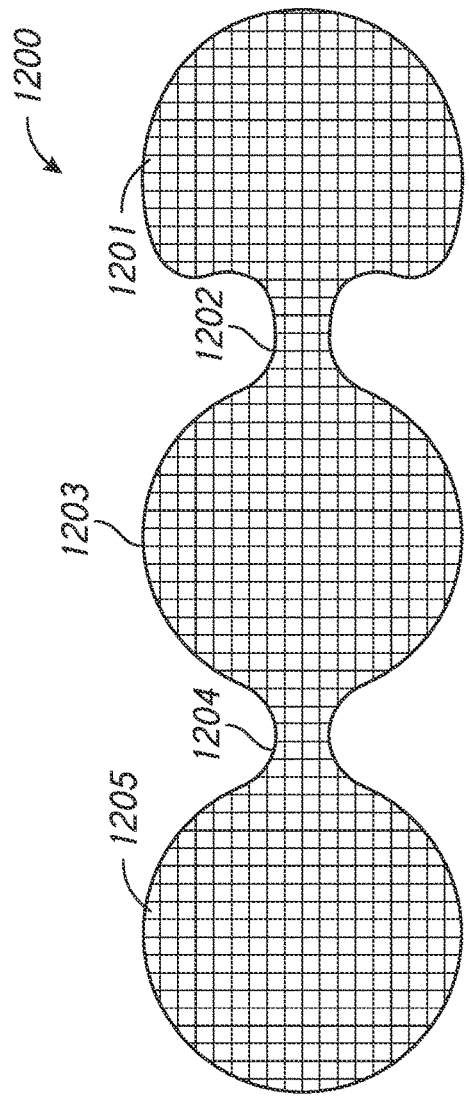
FIGS. 12A and 12B show a schematic depiction of an implant embodiment in a planar state and a formed three-dimensional shape.
Figure 12B:
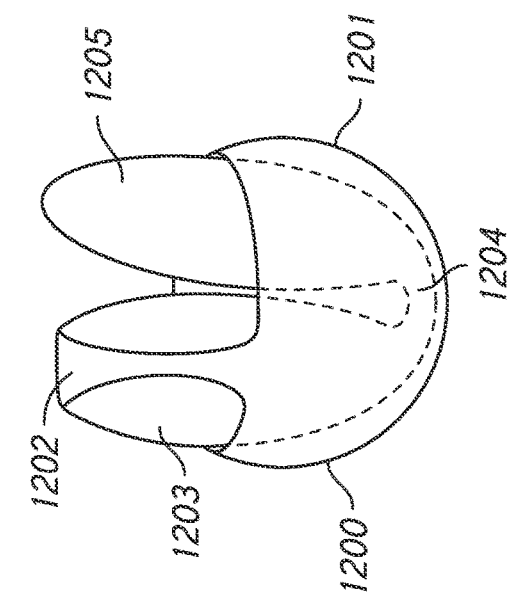

Referring now to FIGS. 12A and 12B, another example of an implant 1200 which, when shaped to a three-dimensional configuration, may include a hemispherical bottom portion 1201 (omitting a hemispherical top portion) and include one or more filler portions 1203 and 1205, respectively interconnected by portions 1202 and 1204 terminating and at least partially filling hemispherical portion 1201 shaped to cover the aneurysm neck entrance, where bottom portion

1201 is greater in diameter than the aneurysm neck entrance. Bottom portion 1201 may be shaped as any hemispherical shape or shape combination, such as: largest planar section 1205 is described by a cord; having a major and minor diameter equal or unequal, with a deflection from an axial centerline to the outer tip of the cord shaping the component to act as a base internal cap at the arterial vessel neck to the entrance of the aneurysm base; and the like.

Figure 11:
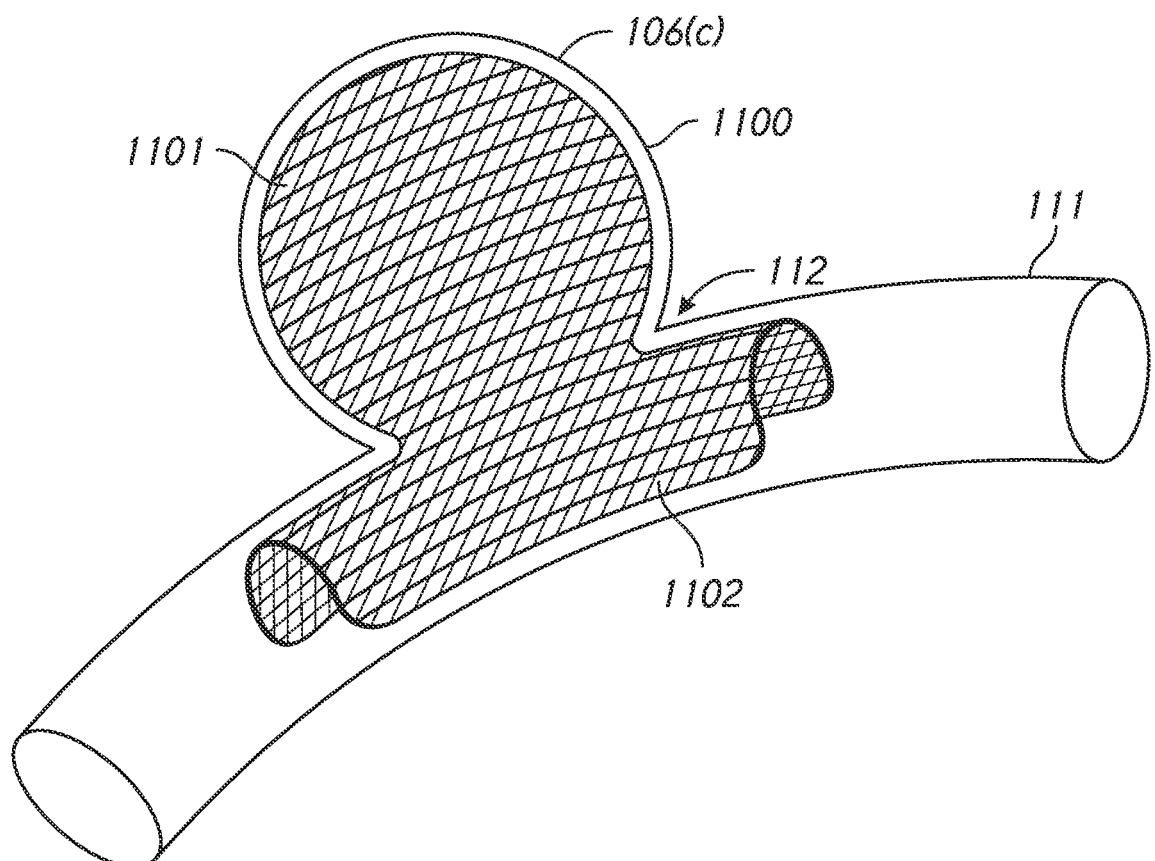
FIG. 11 shows a schematic depiction of an implant embodiment in situ.

Referring now to FIG. 11, the optional addition of an exterior contoured portion 1102 may be continuously connected or fused to the implant which may be configured to cover the aneurysm neck. In the example of FIG. 11, implant 1100 is situated inside aneurysm location 106(*c*) along blood vessel 111, having aneurysm neck 112. The upper portion 1101 of implant 1100 is monolithically attached to lower portion 1102. For the purposes of illustration, lower portion 1102 is shown as a saddle-shaped element, however, lower portion 1102 may be any shape that conforms to at least a portion of the contour of neck 112 such that localized blood flow diversion and stability are provided for in the spirit of the present disclosure. Furthermore, implant 1100 contours may be shaped to the major/minor of the primary vessel and/or aneurysm, and even the radial diameters of not just the aneurysm 106 (*c*) but even neck 112 to optimize the blood flow diversion.

In some of the implant shape variants, implant surface area may be many larger than implant volume, for example, in the case of a spheroid, such a surface area to volume relationship may be managed by the major and minor diameter of the spheroid where the major diameter may be as small as 0.1 mm and the minor diameter may be as small as 0.1 mm (e.g., spherical, partially spherical, elliptical, etc.). The surface area of a surface of the implant may be many times greater than volume, such that portions of the implant overlap each other. The surface area of a surface (one side) of the implant can be at least 1.5 times greater (or at least 2.0 times greater, or at least 2.5 times greater, or at least 3.0 times greater) than an internal volume formed when the implant is in the three-dimensional configuration.

In any of the implant shape variants, various locations along the surfaces of the implant may also include varying thickness at designed points on the inside or outside surface to provide structural support for radial strength or the implant. For example, hemispheres, disks and cords may be shaped with grooves, channels, or rails to add to the structural strength in the radial and axial directions for improved device stiffness and load carrying ability once deployed in situ.

In any of the implant shape variants, there may be reinforcing portions with no porosity. The reinforcing portions may extend at least partially or entirely around a perimeter of the implant. The reinforcing portion may extend at least partially or entirely across a width or length of the implant (e.g., similar to struts). The reinforcing portions may include a same thickness as the porous or mesh portions of the implant.

Figure 3D:
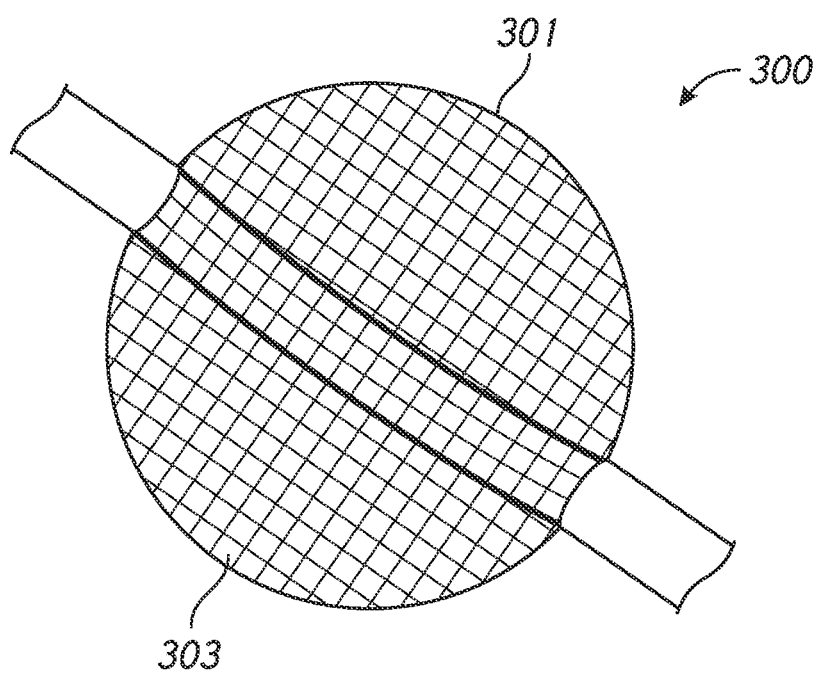
Figure 3E:
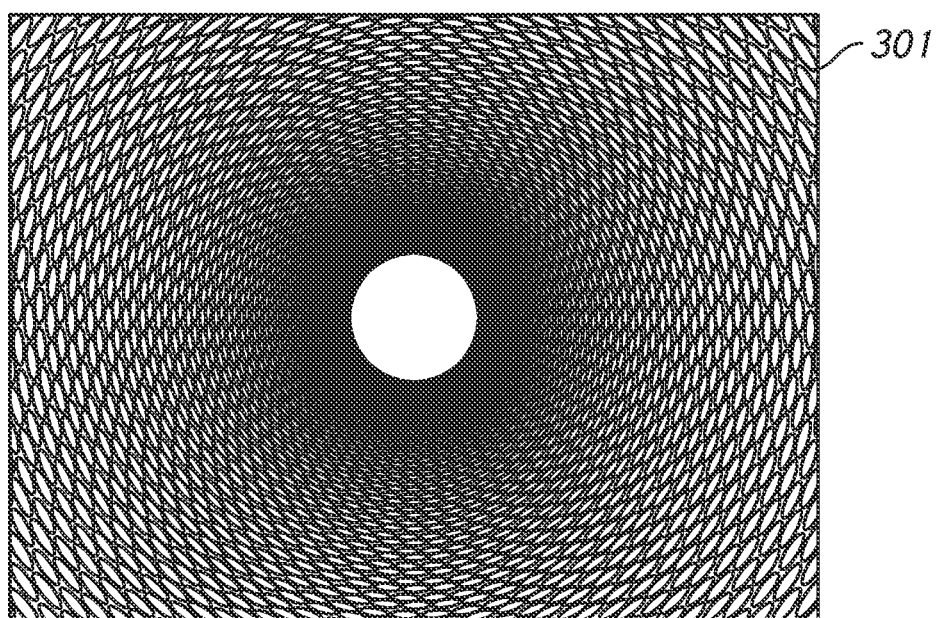

FIGS. 3D and 3E show an exemplar NiTi thin film made in the form of FIGS. 3A-3C. The spheroid implant 300 may be made with one sheet or multiple sheets layered to increase thickness, where shaping can be completed with the sheet(s) layered onto a shaping tool for heat treatment.

In addition to thin film mechanical properties such as material phase and phase transition temperature, residual strain, and mesh structural pattern, further mechanical stiffness may be derived from film thickness from layering of two or more thin film layers, and from formed stiffeners such as pleats or spines and the like. The spines can be used to elongate the thin film material to act as a compression mechanism in reducing the shape set to a different shape that can be placed in a lumen of smaller size then the sphere for delivery to the determined artery site.

Figure 8:
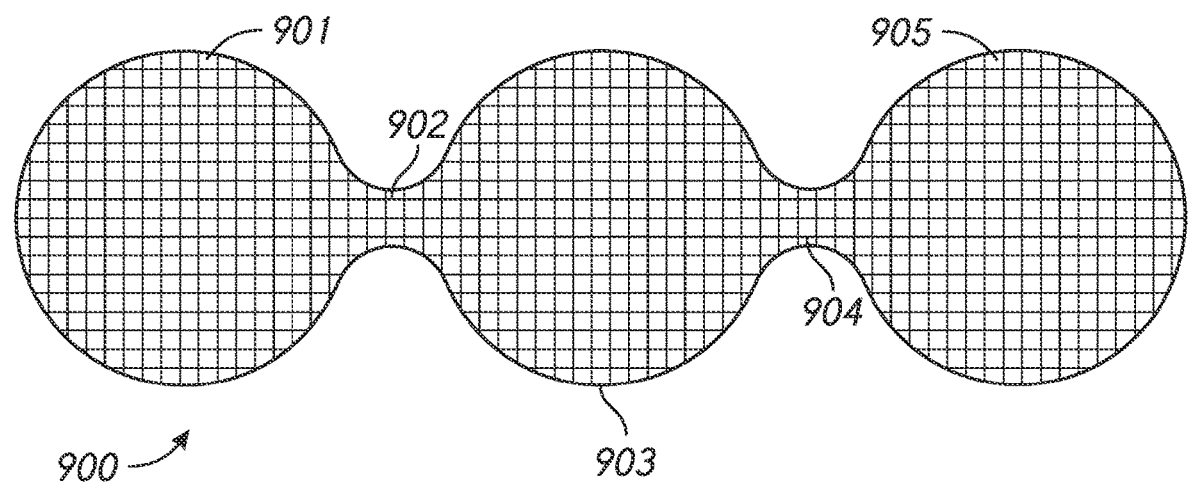
FIG. 8 shows a schematic representation of an embodiment of a NiTi thin film mesh structure in a substantially planar state.
Figure 9:
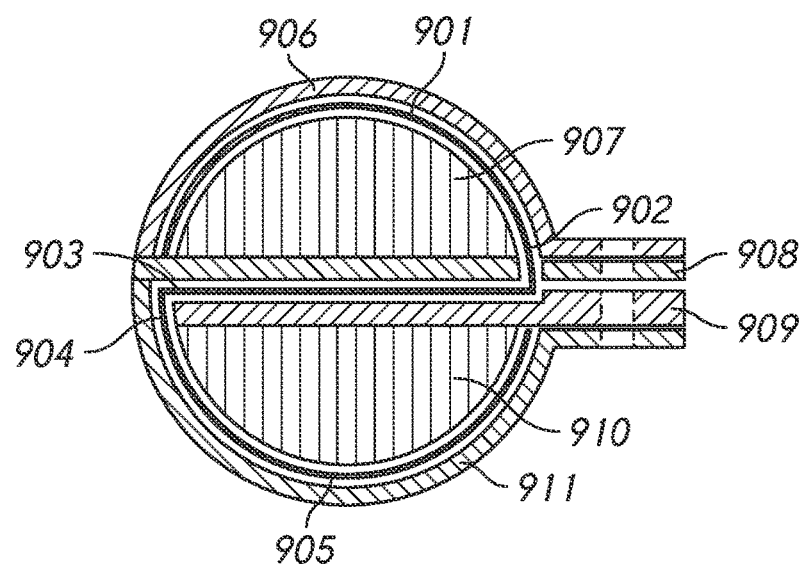
FIG. 9 depicts the embodiment of FIG. 8 during the three-dimensional forming process.

Referring now to FIGS. 8 and 9, another exemplar embodiment is shown. An implant 900 is comprised of a thin film mesh in a substantially flat or planar form having a plurality of segments that may be shaped into a three dimensional form such as a spheroid. An upper segment 901 is joined to a middle segment 903 by connector segment 902, and a lower segment 905 is joined to a middle segment 903 by connector segment 904. Any number of middle segments and connectors may be used to fill and stiffen the central volume of the implant 900, here, a single middle segment 903 with connector segments 902 and 904 are shown for simplicity of communication. Any variety of shape combinations or permutations may be employed, such as: equal major and minor diameters, or unequal major and minor diameters, and the like. The one or more inner segments may also be of any other geometric shape that acts as a volumetric filler within the implant and the aneurysm sac. Most preferably volumetric filling is preferentially positioned nearer the aneurysm neck. In other embodiments, the volumetric filler is a separate component (e.g., a coil).

In FIG. 9 a multi-piece shaping tool is shown shaping upper segment 901, connector segment 902, middle segment 903, connector segment 904, and lower segment 905 into a spheroid shape. A top, outer tool piece 906 sandwiches segment 901 over hemispherical forming piece 907. Connector segment 902 serves as the bending transition to middle segment 903 which is sandwiched between tool pieces 908 and 909. Connector segment 904 serves as the bending transition to lower segment 905 which is sandwiched between lower hemispherical forming piece 910 and bottom outer tool piece 911. The various pieces of the forming tool may be secured together via a threaded hole and screw, an outer clamp, or other such means of mechanical securement prior to the tool and implant 900 being heat treated for shape setting. Heat treatment may occur in a vacuum or non-vacuum inert environment (inert created by using nitrogen, argon or helium gas), fluidized bed, molten salt bath, furnace, or the like, heated to the necessary shaping temperature. For example, the shape setting temperature may be greater than 450 C with subsequent quenching in a cooler media so that the thin film material takes on a 3 dimensional shape. This process may be assisted by wrapping the thin film around tooling or constraining it with wires or other structural elements to conform it to the desired final shape during the forming process. A post descaling or passivation process may be implemented to optimize the surface finish and minimize the possibility of fraction or corrosion.

Corrosion resistance and biocompatibility may be enhanced by placement of an inert micro layer of metallic or non-metallic material at an atomic level, or greater thickness, to ensure of a surface passivation that is robust and can resist corrosion or leach ions into the blood system. The final outer surface may have a final surface finish of material that will be inert to the body and resist corrosion by placing an ionic layer of (Ti) titanium, (Pt) Platinum, (Pd) palladium, (Ir) iridium, (Au) Gold, or other biocompatible metals or may be passivated by the formation of a surface titanium oxide layer. Stainless steel thin films shall be consistent with the medical grade ISO standard requirements of 316, 316L, 316 LVM, 17/7 and any other long term implant materials.

Figure 4A:
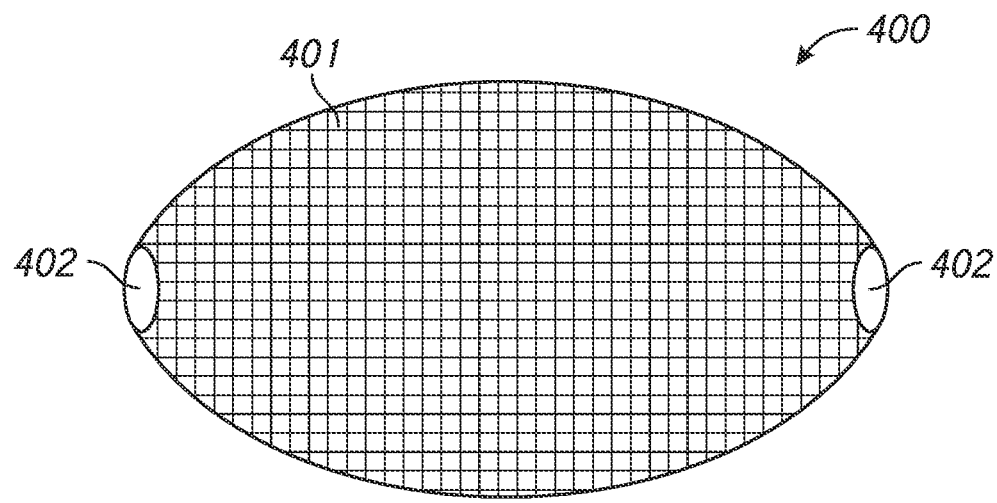
FIGS. 4A and 4B show a schematic depiction of another implant embodiment during its forming process.
Figure 4B:
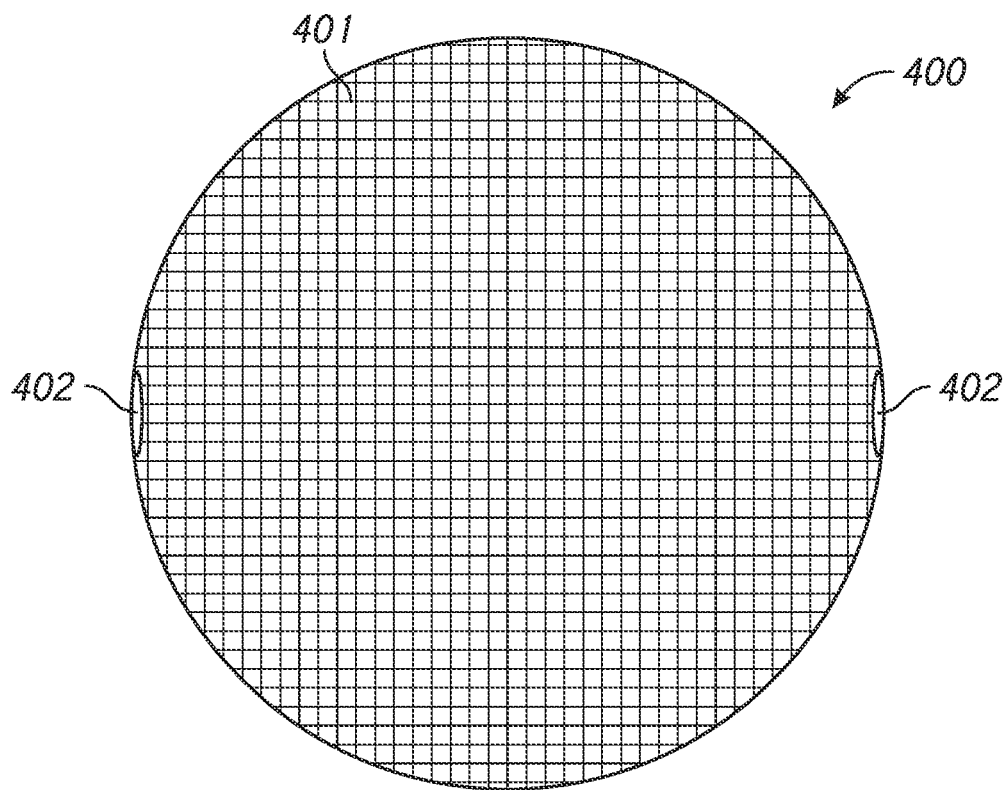

Referring now to FIGS. 4A and 4B, an implant embodiment 400 is shown as being comprised of a thin film mesh 401 formed in a substantially three dimensional state with open ends 402 where a target mandrel would be positioned during the film deposition and patterning processes. Upon further shaping and expansion of mesh 401, implant 400 takes on a three dimensional form of the final implant, a spheroid for example, where some evidence of open ends 402 may remain after shape setting. Referring now to FIGS. 5A-5E, an implant embodiment is described during its forming process, and, during the compression process prior to catheterization.

Implant structure 500 begins in a substantially two dimensional flat or planar form comprised of a plurality of struts with eyelets collectively referred to as element 501 which commonly terminate at a central eyelet 501', the strut structure 501 and 501' being layered over and attached to a thin film mesh 502. Common structural eyelet 501' and individual strut eyelets 501 may be used as part of the three dimensional forming process.

Figure 5A:
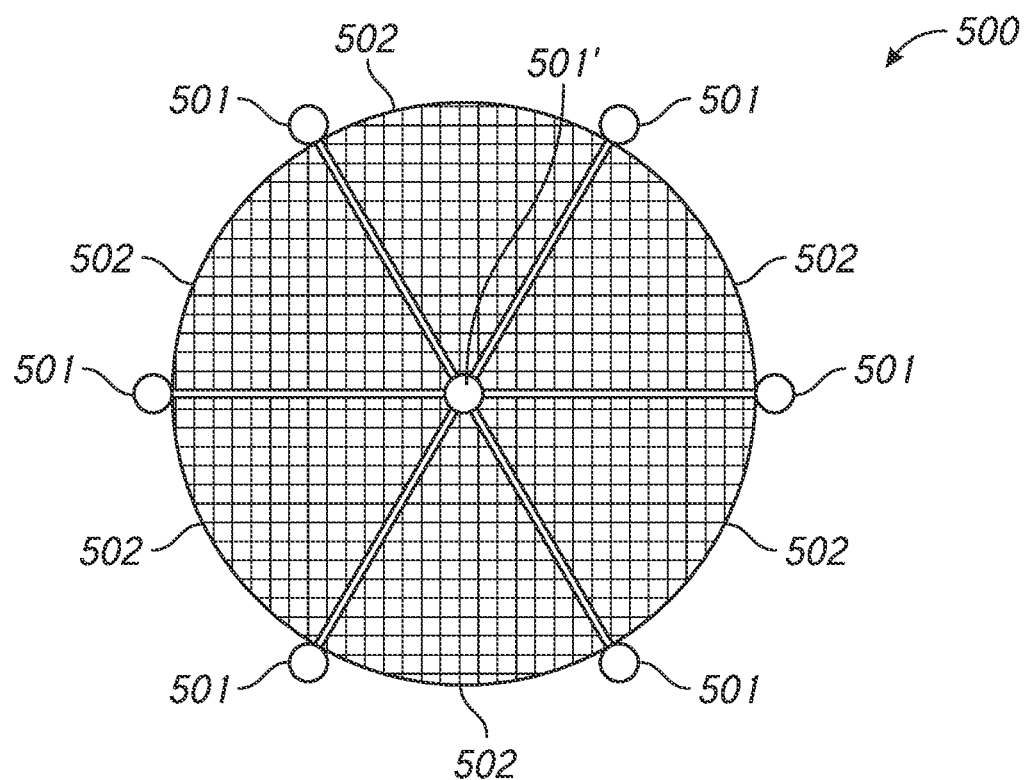
FIGS. 5A-5E show a schematic depiction of yet another implant embodiment during its forming process, and the compression process prior to catheterization.
Figure 5B:
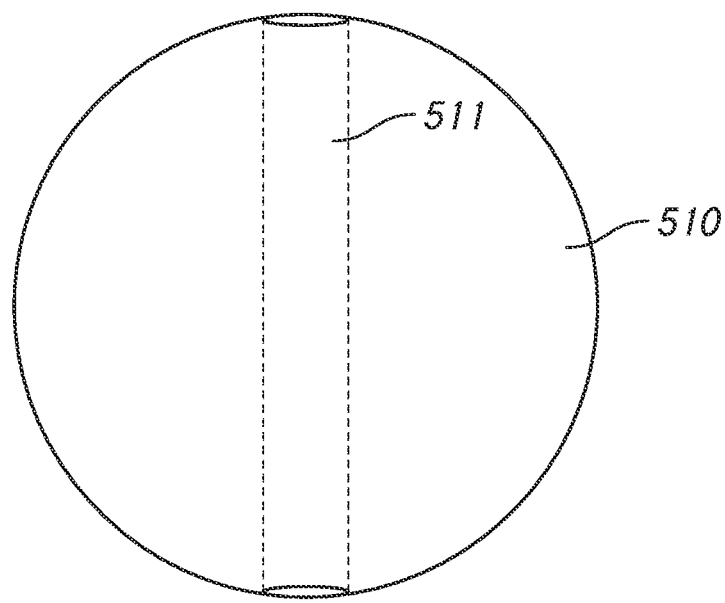
Figure 5C:
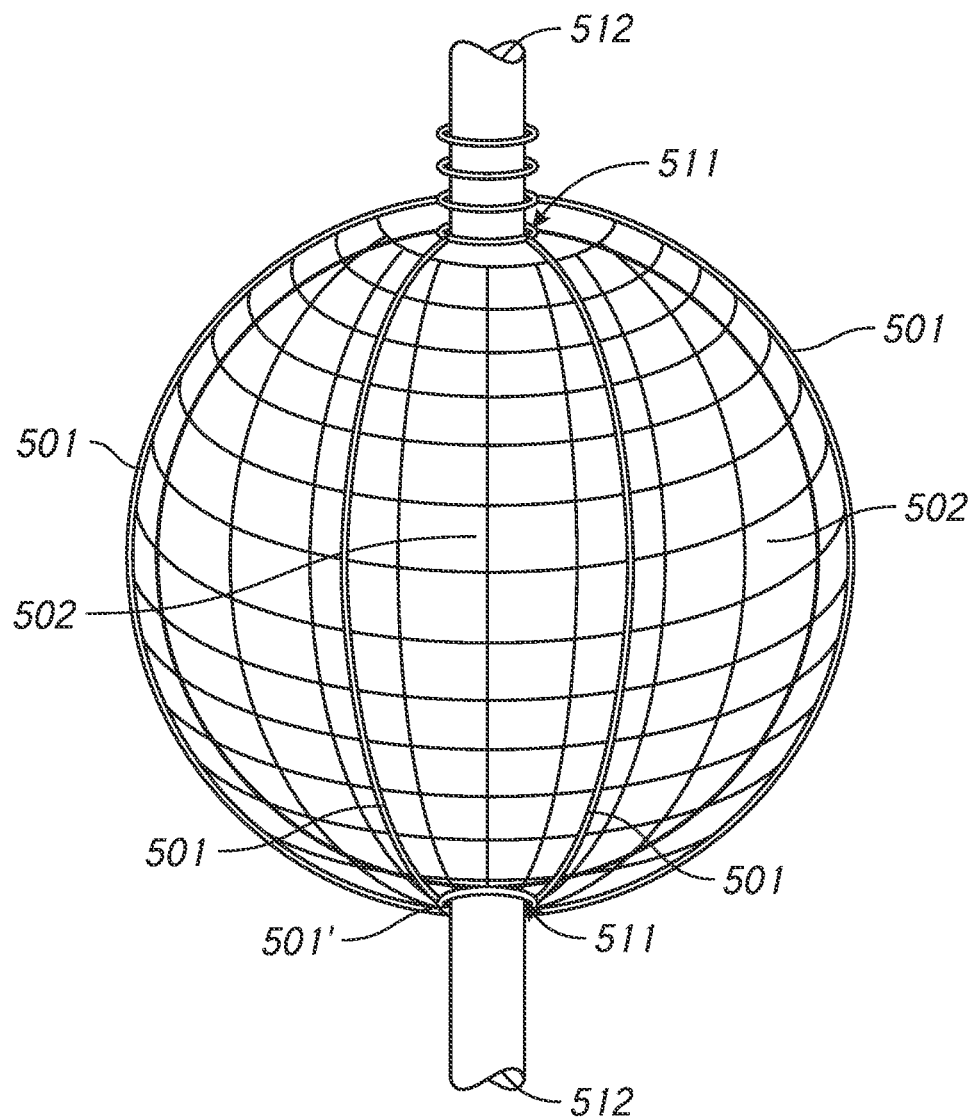

A three dimensional forming tool 510, which for purposes of illustration is a sphere but may be of any shape so desired, may be comprised to include a central passageway 511 through which wire 512 may be passed. As is shown in FIG. 5C, the hole formed by central eyelet 501' may be positioned concentrically with the opening of passageway 511 such that wire 512 may be passed through central eyelet 501' and into passageway 511 in shaping tool 510. The plurality of struts with eyelets 501 may be forced to conform around the outer surface of forming tool 510 and secured in place by positioning the plurality of strut ends with eyelets 501 over the opening of passageway 511 on the opposite end of forming tool 510 before wire 512 is then positioned through eyelets thereby securing them in position to assume a three dimensional shape. Thin film mesh 502 being joined to the plurality of struts 501 also follows the contour of forming tool 510. The joining of mesh 502 to the plurality of struts 501 may be accomplished by laser welding, resistance welding, mechanical crimping, clipping, riveting, and the like, or, may be attached after shape setting heat treatment through means of adhesion by brazing, or chemical bonding. Alternatively, mesh 502 and struts 501 may be formed as an integrated thin film structure.

Figure 5E:
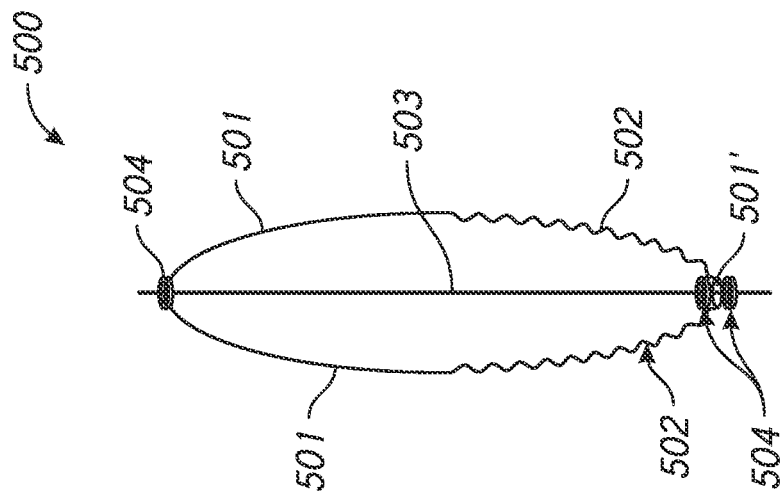
Figure 5D:
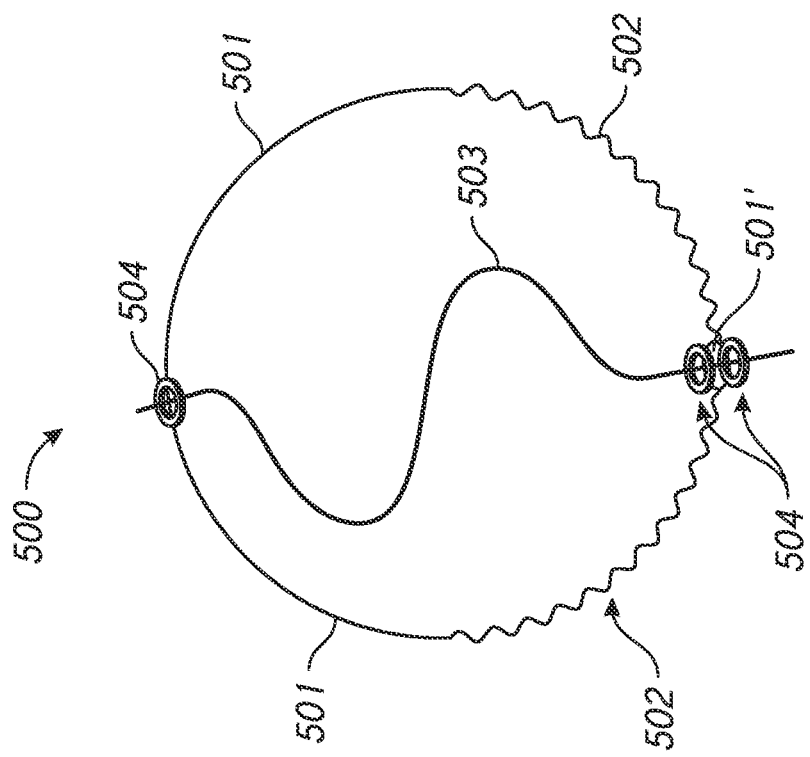

FIGS. 5D and 5E show schematic representations of another embodiment. An optional s-shaped wire segment 503 may be included in the structure of implant 500 to facilitate collapsing its structure for insertion into a catheter. Wire 503 may be comprised of any implant-grade material, with one choice being a wire comprised of shape set NiTi which may be is inserted down the center of implant 500 and fixed in place with metal clips 504 on either end of the plurality of struts 501 and central eyelet 501'. The clips may be of a metal or metal alloy with good x-ray contrast to assist in visualization of the location of the implant while it is being inserted into position, such materials may be selected from any of the groups known in the art such as noble metals, tantalum, palladium, bismuth, and the like. Where galvanic corrosion is of concern, an insulating layer may be used between the surfaces of clips 504 and the surfaces of elements 501 and 501' so as to prevent the formation of a galvanic couple. The size of clips 504 should fit into the inner diameter of the microcatheter that will be used for delivery in vivo. The expanded, three dimensional shape of implant 500 may then be diametrically collapsed by pulling on central wire 503 to stretch the plurality of struts 501 and mesh 502 along the central axis so that it forms a thin oblong structure that will fit into the catheter. When the implant 500 is released from the microcatheter into the aneurysm sac, the entire structure of implant 500 will spring back into its three dimensionally formed shape.

Additionally, a radiopaque marker band (or clip 504) may be made by crimping, bonding or fusing to mesh 502. Mesh 502 may also be configured into a small ball and fused together by energy that initiates a molten state of the material of mesh 502 but controlled by the intensity of energy delivery through means such as laser, acoustic or vibration, and the like.

Figure 6A:
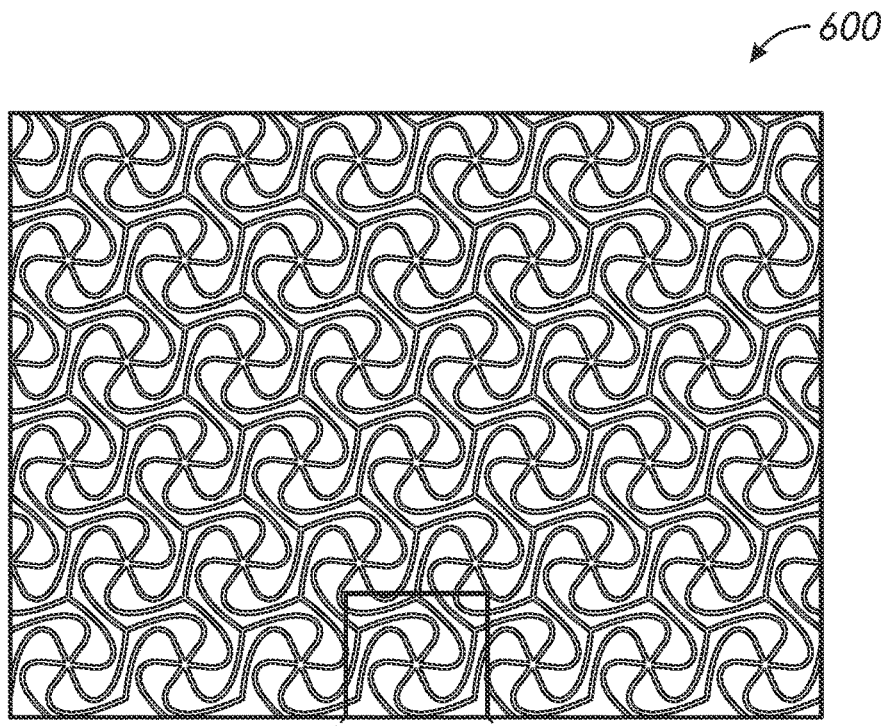
FIGS. 6A and 6B depicts a schematic representation of another embodiment of a NiTi thin film mesh structure and a unit cell thereof.
Figure 6B:
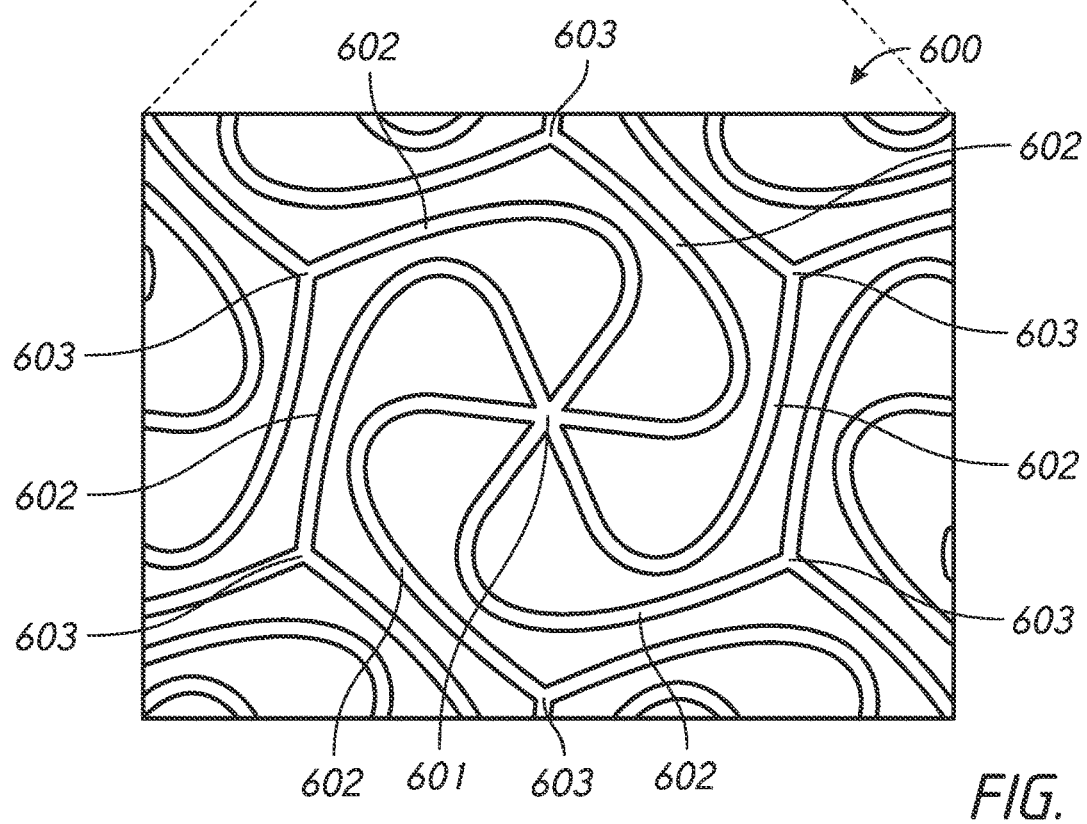

Reference is now made to FIGS. 6A and 6B, which depict a schematic representation of an embodiment of a NiTi thin film mesh structure and a unit cell thereof. The geometry of the NiTi mesh and its mechanical properties are important factors influencing how well the implant performs its variety of functions. The porosity of the mesh 600 may also be generated to provide impedance to blood flow dynamics so as to allow the natural blood clotting mechanism take over to close off the aneurysm.

An outer Titanium atomized layer deposited on the surface of thin film mesh 600 may act as a passivation layer to enhance biocompatibility, or, other surface passivation processes may be used as needed depending on the nature and composition of the mesh structure 600.

Thermomechanical properties of the thin film mesh structure 600 also play an important part of overall implant performance. While any engineering material suitable for permanent implantation may be a constituent comprising the mesh, one particularly suitable material is NiTi. Mesh 600 may be comprised of NiTi in a martensitic phase, austenitic phase, or a phase mixed between the two, or may be a multilayer of several NiTi film compositions. In some embodiments the NiTi thin film may be combined in a multilayer structure with other acceptable biocompatible metals including, but not limited to, biocompatible stainless steel, tantalum, tungsten, titanium, or platinum or combinations or multilayers.

In some embodiments, the mesh 600 of an implant is substantially or predominantly in the austenitic phase so as to provide the best superelasticity and load carrying strength. The greater the difference between body temperature and the temperature at which an implant and the structure of mesh 600 transform into the austenitic stage, the "Af temperature", and the greater the stiffness of the mesh 600. However, with increased stiffness come tradeoffs in fatigue resistance. Therefore, an optimized structure of mesh 600 offers a good combination of thermomechanical properties and mesh geometry to allow for localized distortions during expansion during and after deployment in situ, during manufacturing manipulations, and during catheterized delivery through tortuous vasculature. Af temperatures may range from 10 degrees Celsius to 37 degrees Celsius. The film thickness can be in a range from 1 micron to 200 microns, with a preferable range of about 6 microns to about 12 microns, wherein the thickness is a factor in the outward force and the controlled resistance to compression forces of the applied radial pressure from the blood vessel, a factor in catheter profile, and the like.

The mesh structure 600 of FIGS. 6A and 6B is comprised of a series of arc-like shaped struts 602 connected at a central node 601 that collectively form a "pinwheel". The plurality of struts 602 form a unit cell pinwheel structure that is capable of expansion or contraction. In the instant example, the unit cells of mesh 600 are interconnected by a plurality of secondary nodes 603 that are formed by the intersection of struts 602 of adjacent cells. Thus each unit cell of 600 is connected to an adjacent cell via secondary node 603. The roughly hexagonal shape of the unit cells of mesh 600 allow for a dense packing factor. The expansion or contraction of unit cells induces a rotational deflection that causes struts 602 to either expand or contract about central node 601 allowing the mesh 600 to have a high capacity for dimensional growth, shrinkage, and localized distortion while maintain a high degree of uniformity and density.

Figure 7A:
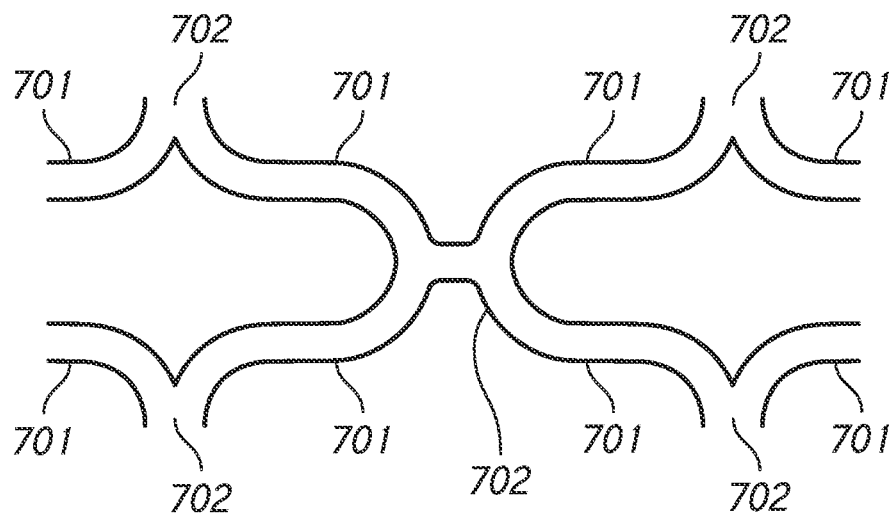
FIGS. 7A-7D depict a schematic representation of embodiments of NiTi thin film mesh structures in a collapsed state and in an expanded state.
Figure 7B:
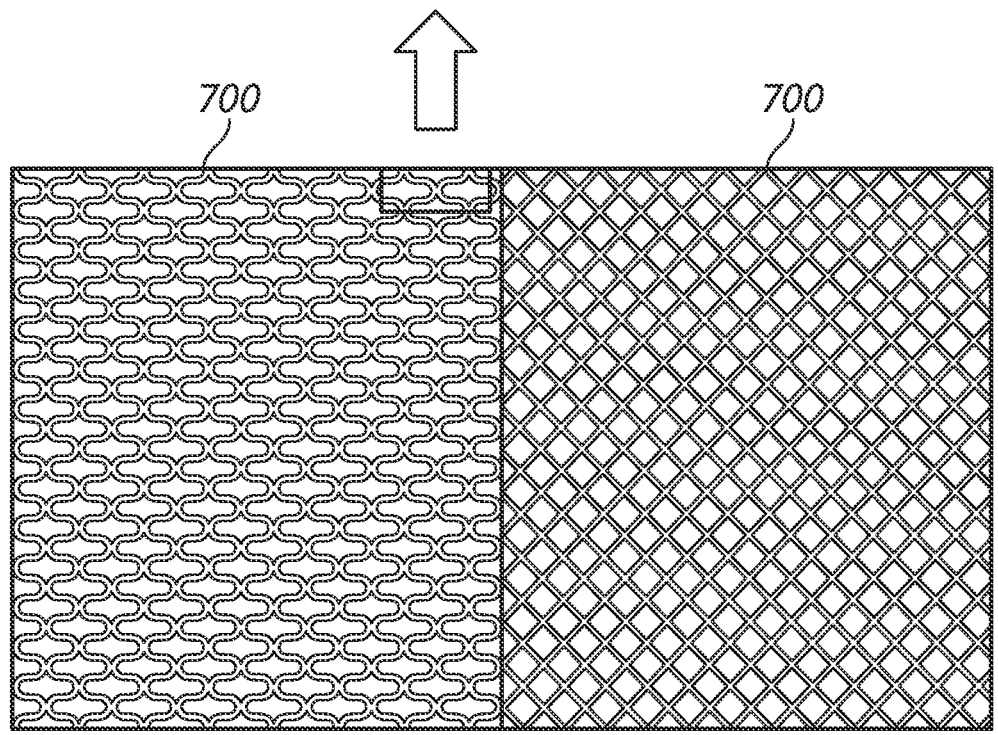
Figure 7C:
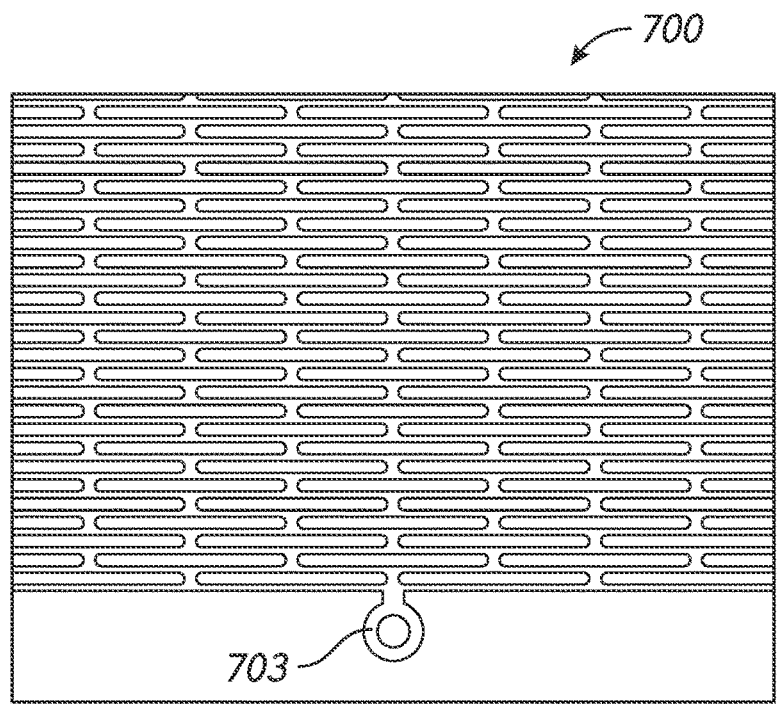
Figure 7D:
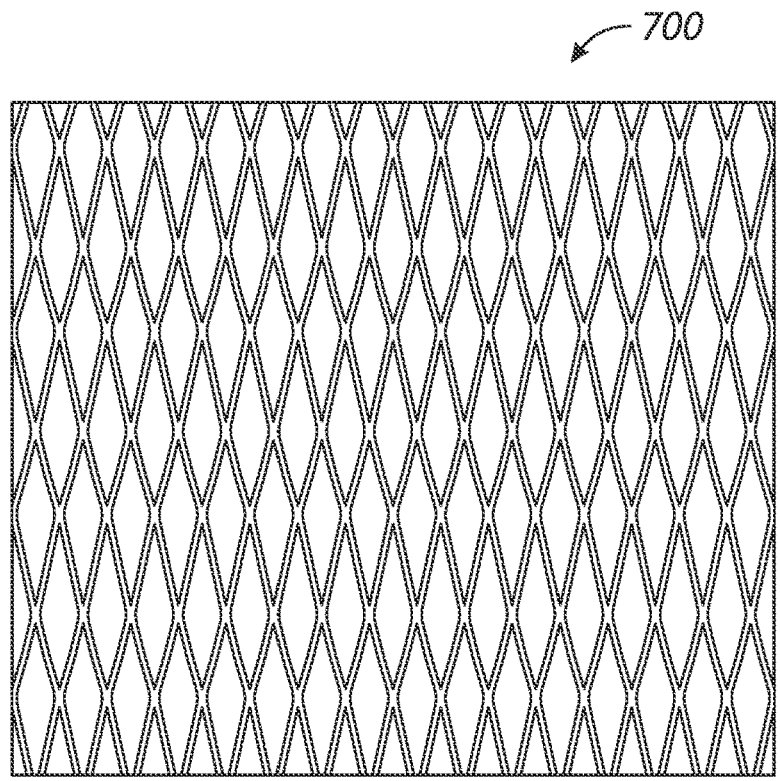

Alternately, and referring now to FIGS. 7A-7D, a simple perforated mesh 700 pattern such as the one shown may be employed. In this exemplar embodiment, a symmetrically repeating plurality of struts 701 are connected to adjacent struts 701 by nodes 702. FIG. 7(a) shows mesh 700 in a generally unexpanded state while FIG. 7(b) shows the same mesh 700 in an expanded state where the plurality of struts 701 and plurality of nodes 702 form a substantially diamond-shaped unit cell. The dimensions of struts 701, nodes 702, and their resultant unit cells may be optimized to provide for the most desired mechanical and porosity characteristics; a variation in the geometry of mesh 700 is shown in FIGS. 7C (unexpanded) and 7D (expanded), the mesh being elongated in one dimensional direction so as to allow for greater expansion and reduced porosity. An optional additional feature for any of the meshes of the present disclosure is an eyelet or "tab" such as the general example shown by element 703. Tab 703 may be used to convenience during manufacturing manipulation, for attachment of radiopaque markers, as a sacrificial surface for joining by welding, as a marker visible in the implantation procedure by x-ray or other methods for placement and location confirmation, and the like.

Any of the embodiments described herein may include radiopaque marker bands that can be made from tantalum, titanium or precious metal and placed on the occluder at any specific location where an eyelet or nodule is formed by the thin film process or configuring the thin film into a thicker section then the standard wall thickness. The marker may be crimped, swaged, fused or adhered to the eyelet or the frame based on the optimum location for the identification of placement of the occlude in the body by x-ray (fluoroscopy). The marker may also be plated onto the specific location or dip plated to ensure the patency of a specific area of the Occluder is visible under fluoroscopy. Alternatively, radiopacity may be achieved by adding high brightness metals either as a surface coating or by inclusion into a multilayer structure in such amounts that do not compromise the shaping of the material into desired 3 dimensional forms or its mechanical robustness as required for successful deployment.

The occluder shall be sized based on the fluoroscope sizing and then the appropriate size for treatment shall selected by the neurovascular surgeon. The device shall be preloaded with the specific occlude and sterilized by means of gamma, e-beam or ETO, without impacting the overall device capability for a one-time-use and achieving the trackability to the specific location without any friability to the delivery system or the occlude. Once in position, confirmed by the neurovascular surgeon by fluoroscopy, the center delivery wire can be manipulated by torque and axial pushing to ensure the delivery system tip is at the neck of the aneurysm area. The release shall be completed by moving the inner delivery wire distally, or by moving the outer sheath proximally or by both at the same time. The occluder shall change from the configured loaded shape to the final configured shape partially as it exits the sheathed state but will achieve its final shape once fully released from the delivery system.

Figure 13A:
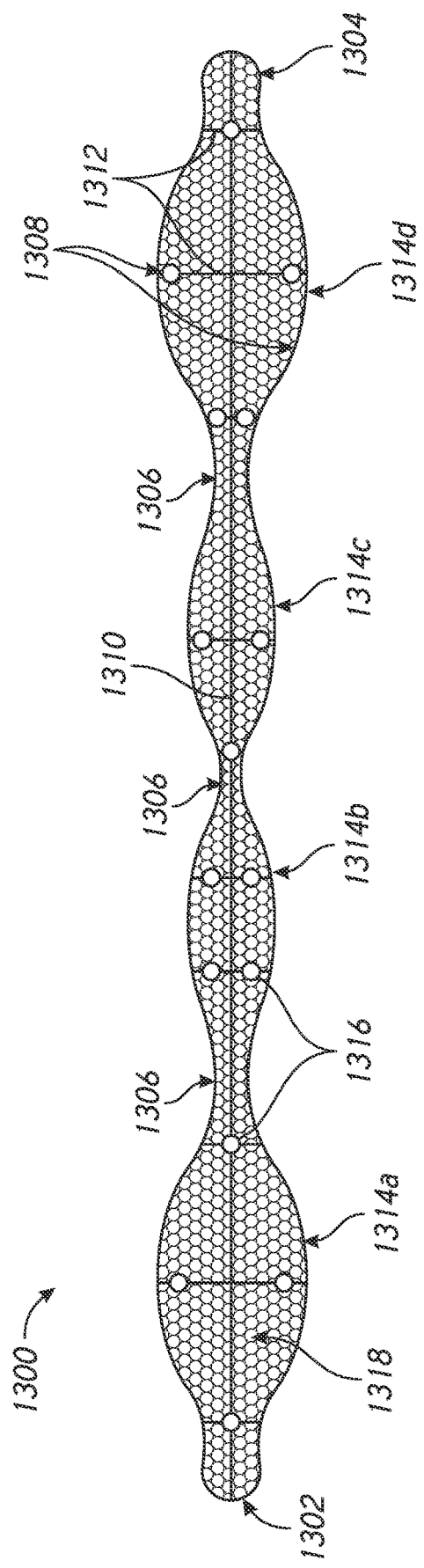
FIGS. 13A to 13D show yet another implant embodiment in a planar state and a partially cylindrical shape.
Figure 13B:
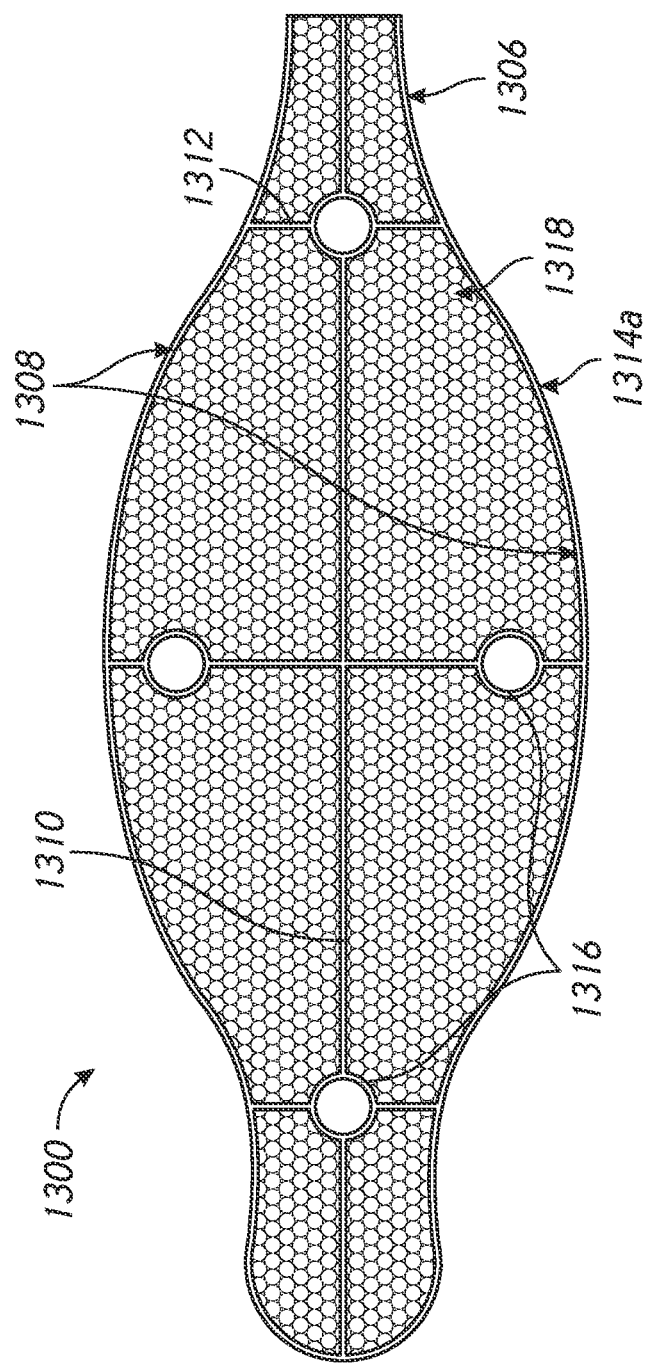
Figure 13C:
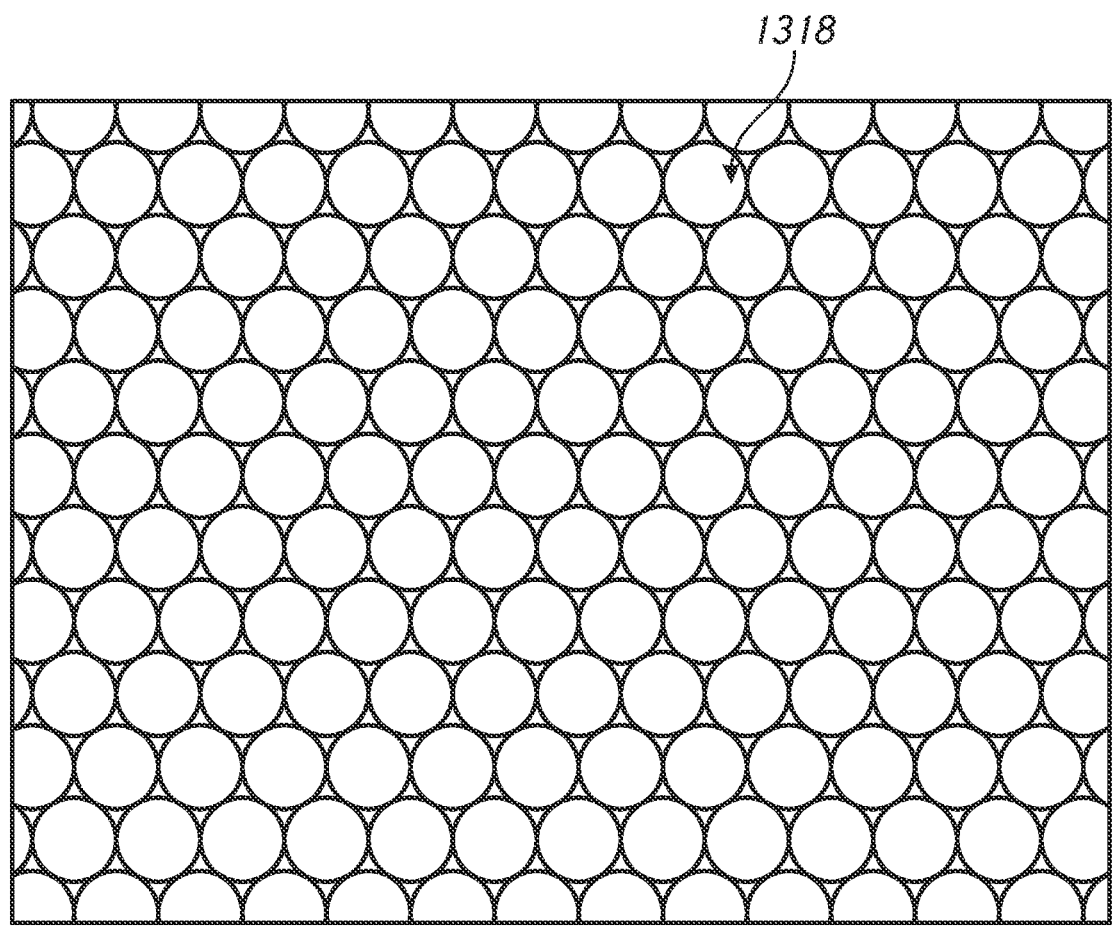
Figure 13D:
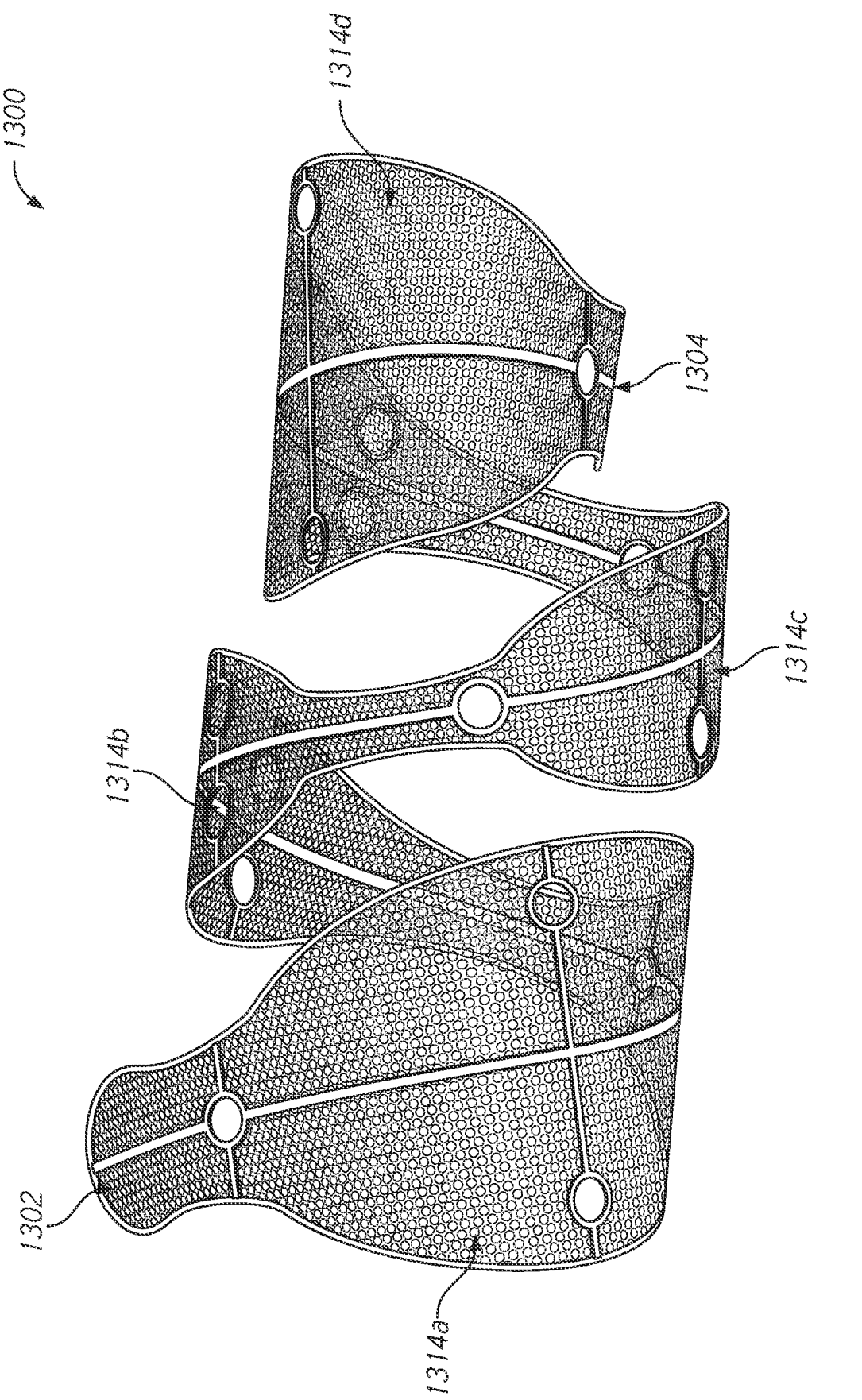

FIGS. 13A-13D show another embodiment of an occlusion device 1300 that is configured to transition between a first, two-dimensional configuration (see FIG. 13A) and a second, three-dimensional configuration (see FIG. 13D). In some configurations, the occlusion device can be constructed from thin-film nitinol.

The occlusion device includes a mesh structure having a porosity 1318 with a substantially uniform or uniform pore size (see FIG. 13C). Any single pore size can be within at least about 5% of a pore size of any other pore or the mean pore size. The size of the perforation holes and the dimensions of the supporting mesh are chosen to maximize the occlusive performance in the device while maintaining sufficient structural strength to enable handling and deployment of the device without tearing.

In the first configuration, the occlusion device 1300 is in a flat, planar configuration with parallel surfaces. At rest, the occlusion device 1300 has a substantially uniform or uniform thickness, for example, a thickness of the occlusion device 1300 is at least about 0.2 mils and/or less than or equal to about 2.0 mils, such as between about 0.5 mils to about 1.5 mils or between about 1.0 mils to about 2.0 mils.

As shown in FIG. 13A, the occlusion device 1300 extends from a first end portion 1302 to a second end portion 1304. The occlusion device can include one or more petals or segments 1314a-1314d (e.g., at least two, at least three, at least four, or more) extending along a longitudinal axis of the occlusion device 1300. The one or more segments 1314a-1314d can be arranged such that a longitudinal axis of each of the one or more segments 1314a-1314d extends along a longitudinal axis of the occlusion device 1300.

A length of each segment 1314a-1314d can be greater than a width of the respective segment 1314a-1314d. The length of each segment 1314a-1314d can be at least about 1.5×, at least about 2.0×, at least about 2.5×, or at least about 3.0× greater than the width of the respective segment 1314a-1314d.

One or more of the segments 1314a-1314d can be the same size and/or be differently sized from one or more other segments 1314a-1314d. For example, in some configurations, the segments 1314a-1314d can be the same size. In other configurations, each of the segments can be differently sized. In yet other configurations, a subset of the segments can be differently sized from another subset of the segments.

For example, as shown in FIG. 13A, segments 1314a, 1314d can be larger than segments 1314b, 1314c. Smaller segments 1314b, 1314c can be positioned longitudinally between larger segments 1314a, 1314d. The length and/or width of segments 1314a, 1314d can be greater than the length and/or width of segments 1314b, 1314c. As shown, the lengths and the widths of segments 1314a 1314d are greater than the lengths and the widths of segments 1314b, 1314c.

The length and/or width of each segment 1314a-1314d can be greater than the length and/or width of first and/or second end portions 1302, 1304. As shown, a length and width of each segment 1314a-1314d is greater than the length and width of first and second end portions 1302, 1304.

The occlusion device 1300 can be formed as a monolithic structure with each of the segments 1314a-1314d joined by connecting portions 1306. The length and/or width of each segment 1314a-1314d can be greater than the length and/or width of each connecting portions 1306.

The occlusion device can include reinforcing portions with no porosity to provide smooth edges and structural support. The reinforcing portions can have the same thickness as the porous portions of the occlusion device. The reinforcing portions can be monolithically formed with the porous portions.

The occlusion device can have peripheral reinforcing portions 1308, horizontal reinforcing portions 1310, and/or vertical reinforcing portions 1312. Each reinforcing portion 1308, 1310, 1312 can have a width of at least about 0.2 mil and/or less than or equal to about 1 mil, such as between about 0.2 mil and about 0.5 mil or between about 0.5 mil and about 1.0 mil.

Peripheral reinforcing portions 1308 can extend at least partially or entirely around a periphery of the occlusion device 1300. A horizontal reinforcing portion 1310 can extend at least partially or entirely across the longitudinal axis of the occlusion device 1300. One or more vertical reinforcing portions 1308 can extend perpendicular to the longitudinal axis of the occlusion device 1300. For example, a vertical reinforcing portion 1308 can extend across a central axis of a segment (see e.g., segments 1314a, 1314c, 1314d), or multiple vertical reinforcing portions 1308 can extend parallel to each other in a single segment (see, e.g., segment 1314b).

Optionally, the occlusion device 1300 can have one or more holes 1316 for use as grommets to facilitate attachment of support wires or other structures for delivery. Each hole 1316 can be centered on a horizontal reinforcing portion 1310 and/or vertical reinforcing portion 1308. Each of the holes 1316 can have a larger open area than a pore of the porous portion 1318.

The occlusion device 1300 can be shape-set such that the occlusion device 1300 can transition from the two-dimensional configuration to the three-dimensional configuration. In the three-dimensional configuration, the occlusion device 1300 forms a volumetric filler. As shown in FIG. 13D, the occlusion device 1300 can spiral to form a cylindrical form with open ends.

When transformed from the two-dimensional configuration to the three-dimensional configuration, the pore size or open area of each pore in the three-dimensional configuration changes less than 20% (or less than 15%, or less than 10%, or less than 5%) than the pore size or open area of the same pore in the two-dimensional configuration. In each of the two-dimensional and three-dimensional configurations, there is less than 20% (or less than 15% or less than 10% or less than 5%) variation between the pore size or open area of any two openings. In each of the two-dimensional configuration and the three-dimensional configuration, there is less than 20% (or less than 15% or less than 10% or less than 5%) variation or between the pore size of any opening and the mean pore size of the entire porosity. In some configurations, every pore and opening has a uniform size in the two-dimensional configuration and/or three-dimensional configuration.

The surface area of a surface (one side) of the implant can be at least 1.5 times greater (or at least 2.0 times greater, or at least 2.5 times greater, or at least 3.0 times greater) than an internal volume formed when the implant is in the three-dimensional configuration.

Figure 14A:
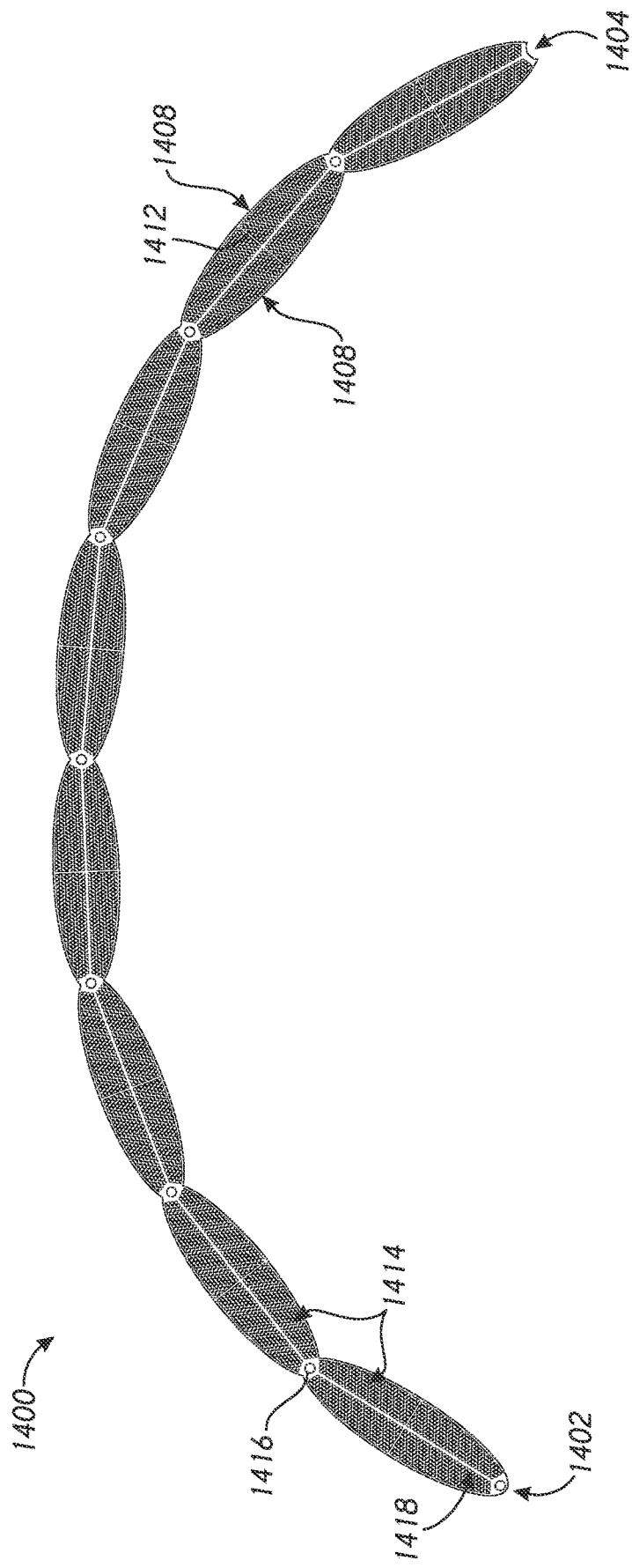
FIGS. 14A to 14D show yet another implant embodiment in a planar state and a partially spherical shape.
Figure 14B:
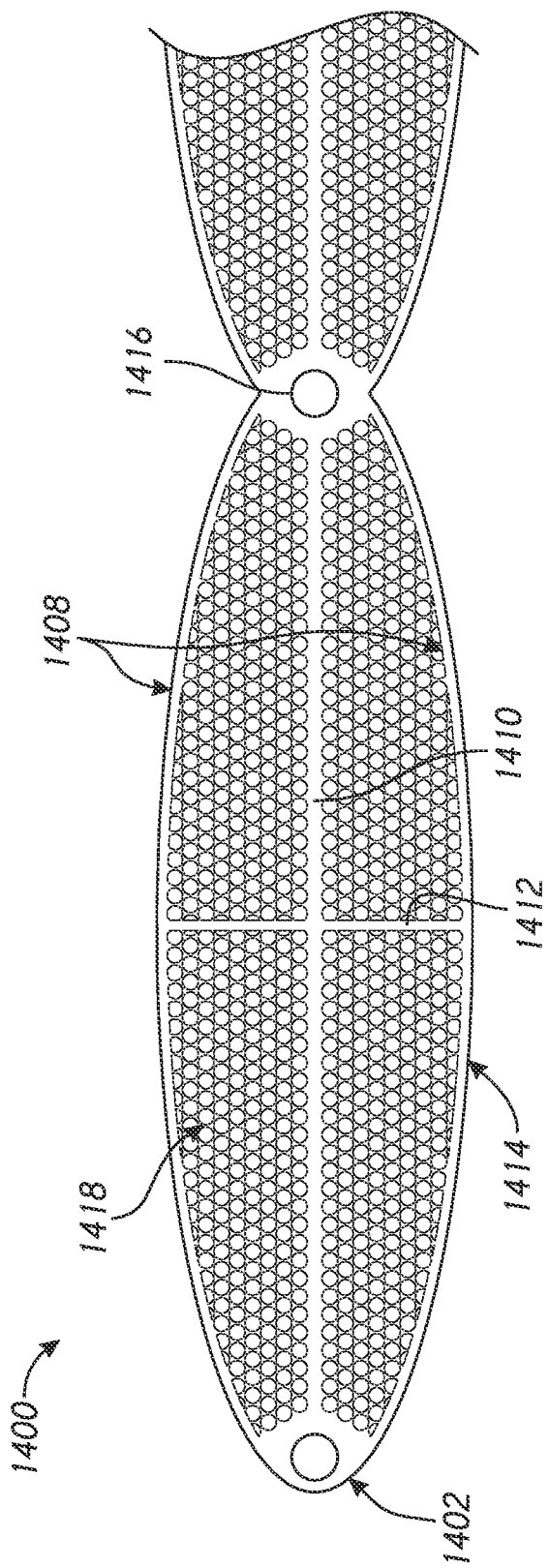
Figure 14C:
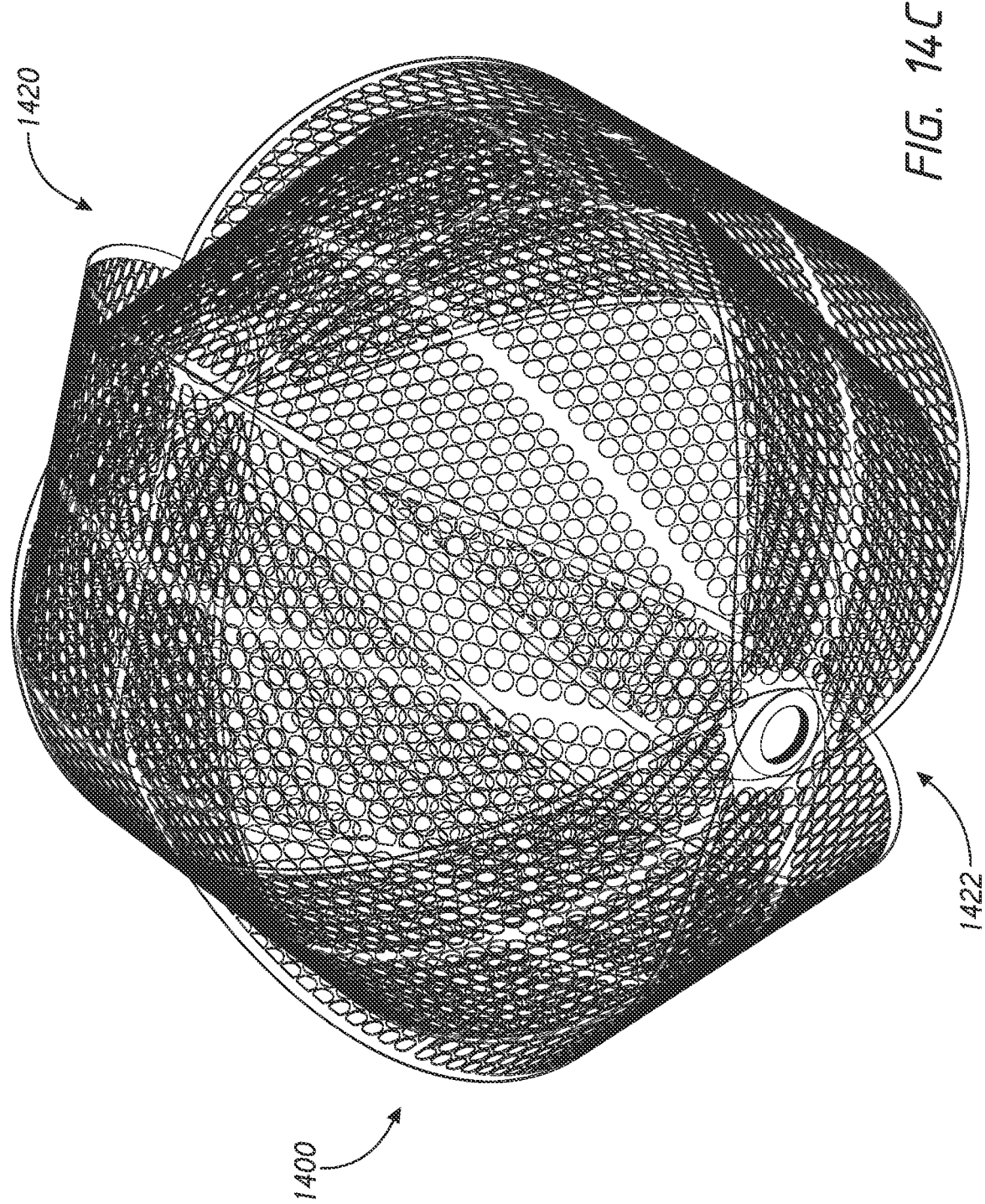
Figure 14D:
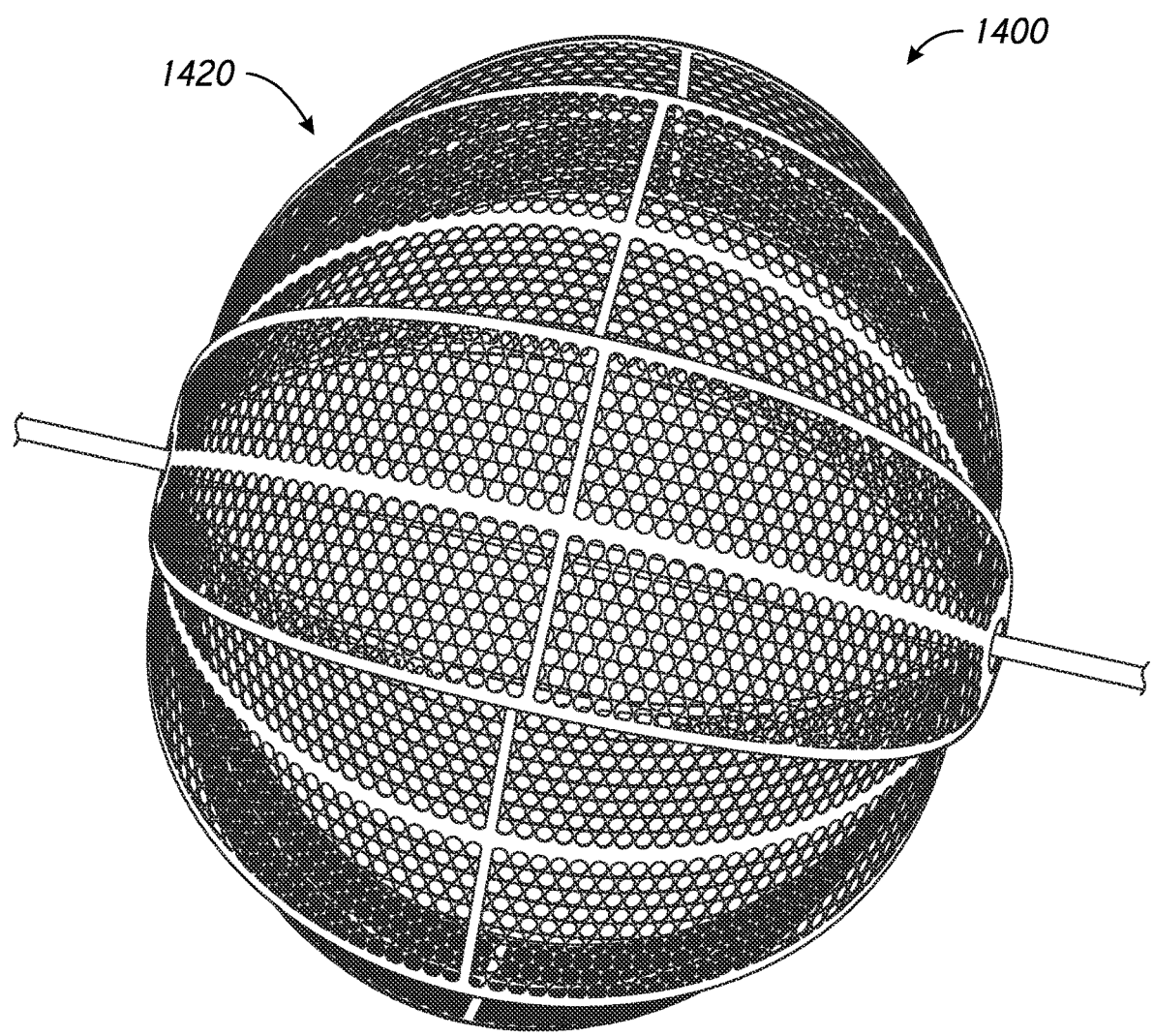

FIGS. 14A-14D show yet another embodiment of an occlusion device 1400 that is configured to transition between a first, two-dimensional configuration (see FIG. 14A) and a second, three-dimensional configuration (see FIGS. 14C and 14D). In some configurations, the occlusion device can be constructed from thin-film nitinol.

The occlusion device includes a mesh structure having a porosity 1418 with a substantially uniform or uniform pore size (see FIG. 14B). Any single pore size can be within at least 5% of a pore size of any other pore or the mean pore size. The size of the perforation holes and the dimensions of the supporting mesh are chosen to maximize the occlusive performance in the device while maintaining sufficient structural strength to enable handling and deployment of the device without tearing.

In the first configuration, the occlusion device 1400 is in a flat, planar configuration with parallel surfaces. At rest, the occlusion device 1400 has a substantially uniform or uniform thickness. For example, a thickness of the occlusion device 1300 can be at least about 0.2 mils and/or less than or equal to about 2.0 mils, such between about 0.5 mils and about 1.5 mils or between about 1.0 mils and about 2.0 mils.

As shown in FIG. 14A, the occlusion device 1400 extends from a first end 1402 to a second end 1404. The occlusion device 1400 can include one or more petals or segments 1414 (e.g., at least two, at least three, at least four, or more) connected end-to-end. The one or more segments 1414 may be arranged such that segments are arranged at an angle with respect to adjacent segments. However, in other configurations, a longitudinal axis of each segment 1414 can extend along a longitudinal axis of the occlusion device 1400.

A length of each segment 1414 can be greater than a width of the respective segment 1414. The length of each segment 1414 can be at least about 1.5×, at least about 2.0×, at least about 2.5×, or at least about 3.0× greater than the width of the respective segment 1414.

As shown, each of the segments 1414 is the same size with equal lengths and widths. However, in other configurations, one or more of the segments 1414 can be differently sized from one or more other segments 1414.

The occlusion device 1400 can be formed as a monolithic structure with each of the segments 1414 joined to an adjacent segment. Optionally, the occlusion device 1400 can include a hole or grommet 1416 at a transition between adjacent segments. Each of the holes 1416 can have a larger open area than a pore of the porous portion 1418. The holes 1416 can be used to facilitate attachment to support wires or other structures for delivery.

The occlusion device 1400 can include reinforcing portions with no porosity to provide smooth edges and structural support. The reinforcing portions can have the same thickness as porous portions of the occlusion device. The reinforcing portions can be monolithically formed with the porous portions.

The occlusion device can have peripheral reinforcing portions 1408, horizontal reinforcing portions 1410, and/or vertical reinforcing portions 1412. Each reinforcing portion 1408, 1410, 1412 can have a width of at least about 0.2 mil and/or less than or equal to about 1 mil, such as between about 0.2 mil and about 0.5 mil or between about 0.5 mil and about 1.0 mil.

Peripheral reinforcing portions 1408 can extend at least partially or entirely around a periphery of the occlusion device 1400. A horizontal reinforcing portion 1410 can extend at least partially or entirely across the longitudinal axis of one or more segments 1414. One or more vertical reinforcing portions 1408 can extend perpendicular to the longitudinal axis of one or more segments 1414. For example, a vertical reinforcing portion 1418 can extend across a central axis of each segment 1414.

The occlusion device 1400 can be shape-set such that the occlusion device 1400 can transition from the two-dimensional configuration to the three-dimensional configuration. As shown in FIGS. 14C and 14D, the occlusion device 1400 can include a closed portion 1420 and an open portion 1422. The occlusion device 1400 can fold such that a longitudinal dimension of each segment can extend from one side of the open portion 1422 and around to the other side of the open portion 1422 to form the closed portion 1420. The open portion 1422 can be formed by the longitudinal edges of two adjacent segments (see FIG. 14C). When completely folded, adjacent longitudinal edges of segments 1414 overlap each other such that there are no gaps between adjacent segments 1414 (see FIG. 14D).

When transformed from the two-dimensional configuration to the three-dimensional configuration, the pore size or open area of each pore in the three-dimensional configuration changes less than 20% (or less than 15%, or less than 10%, or less than 5%) than the pore size or open area of the same pore in the two-dimensional configuration. In each of the two-dimensional configuration and the three-dimensional configuration, there is less than 20% (or less than 15% or less than 10% or less than 5%) variation between the pore size or open area of any two openings. In each of the two-dimensional configuration and the three-dimensional configuration, there is less than 20% (or less than 15% or less than 10% or less than 5%) variation or between the pore size of any opening and the mean pore size of the entire porosity. In some configurations, every pore and opening has a uniform size in the two-dimensional configuration and/or three-dimensional configuration.

The surface area of a surface (one side) of the implant can be at least 1.5 times greater (or at least 2.0 times greater, or at least 2.5 times greater, or at least 3.0 times greater) than an internal volume formed when the implant is in the three-dimensional configuration.

When implanted, the open portion 1422 can face the aneurysm neck such that blood can flow into the internal volume formed by the closed portion 1420. In some embodiments, fillers (e.g., coils) can be released in the internal volume of the occlusion device 1400.

Although certain embodiments have been described herein with respect to neurovascular aneurysms, the devices described herein can be used to treat other types of aneurysms, e.g. aortic aneurysms, ventricular aneurysms, etc.

As used herein, the relative terms "proximal" and "distal" shall be defined from the perspective of the delivery system. Thus, proximal refers to the direction of the handle portion of the delivery system and distal refers to the direction of the distal tip.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 100 microns" includes "100 microns." Phrases preceded by a term such as "substantially" include the recited phrase and should be interpreted based on the circumstances (e.g., as much as reasonably possible under the circumstances). For example, "substantially uniform" includes "uniform."

EXAMPLE EMBODIMENTS

The following example embodiments identify some possible permutations of combinations of features disclosed herein, although other permutations of combinations of features are also possible.

1. An occlusion device comprising:
   a mesh structure comprising a first surface and a second surface, at least a portion of the mesh structure comprises porosity, the mesh structure being configured to transition between a two-dimensional configuration and a three-dimensional configuration,
   wherein in the two-dimensional configuration and at rest, the first surface is parallel to the second surface, and
   wherein in the three-dimensional configuration, the occlusion device comprises an internal volume.

2. The occlusion device of Embodiment 1, wherein the mesh structure is a monolithic sheet.

3. The occlusion device of Embodiment 1 or 2, wherein the mesh structure comprises a thickness of no more than 0.002 inches.

4. The occlusion device of any one of Embodiments 1 to 3, wherein in the three-dimensional configuration, the occlusion device is at least partially spherical.

5. The occlusion device of any one of Embodiments 1 to 3, wherein in the three-dimensional configuration, the occlusion device is at least partially cylindrical.

6. The occlusion device of any one of the preceding Embodiments, wherein the mesh structure comprises a uniform thickness.

7. The occlusion device of any one of the preceding Embodiments, wherein a surface area of the first surface is at least 2× greater than the internal volume.

8. The occlusion device of Embodiment 7, wherein the surface area of the first surface is at least 3× greater than the internal volume.

9. The occlusion device of any one of the preceding Embodiments, wherein the mesh structure comprises a reinforcing portion with no porosity.

10. The occlusion device of Embodiment 9, wherein the reinforcing portion extends around a periphery of the mesh structure.

11. The occlusion device of Embodiment 10, wherein the reinforcing portion extends around the entire periphery of the mesh structure.

12. The occlusion device of any one of the preceding Embodiments, wherein in the three-dimensional configuration, the occlusion device has an open portion to provide access to the internal volume.

13. The occlusion device of any one of the preceding Embodiments, wherein in the two-dimensional configuration, the entire porosity has a uniform pore size.

14. The occlusion device of any one of the preceding Embodiments, wherein in the two-dimensional configuration, any pore size of the porosity is within 10 percent of a first mean pore size of the entire porosity of the two-dimensional configuration.

15. The occlusion device of Embodiment 14, wherein in the two-dimensional configuration, any pore size of the porosity is within 5 percent of the first mean pore size.

16. The occlusion device of any one of the preceding Embodiments, wherein in the three-dimensional configuration, any pore size of the mesh structure is within 10 percent of a second mean pore size of the entire porosity of the two-dimensional configuration.

17. The occlusion device of Embodiment 16, wherein a first pore size of any pore in the two-dimensional configuration is within 5 percent of a second pore size of the same pore in the three-dimensional configuration.

18. The occlusion device of any one of the preceding Embodiments, wherein in the three-dimensional configuration, the mesh structure is partially austenitic and partially martensitic.

19. The occlusion device of claim 18, wherein the mesh structure is more austenitic than martensitic.

20. The occlusion device of any one of the preceding Embodiments, further comprising a volumetric filler disposed in the internal volume of the mesh structure.

21. The occlusion device of Embodiment 20, wherein mesh structure comprises the volumetric filler.

22. An occlusion device comprising:
a monolithic structure comprising porosity, the monolithic structure being configured to transition between a first configuration and a second configuration,
wherein in the first configuration, any pore size of the porosity is within 10 percent of a first mean pore size of the entire porosity of the first configuration;
wherein in the second configuration, any pore size of the porosity is within 10 percent of a second mean pore size of the entire porosity of the second configuration.

23. The occlusion device of Embodiment 22, wherein the monolithic structure is a monolithic sheet.

24. The occlusion device of Embodiment 22 or 23, wherein the monolithic structure comprises a thickness of no more than 0.002 inches.

25. The occlusion device of any one of Embodiments 22 to 24, wherein in the second configuration, the occlusion device is at least partially spherical.

26. The occlusion device of any one of Embodiments 22 to 24, wherein in the second configuration, the occlusion device is at least partially cylindrical.

27. The occlusion device of any one of Embodiments 22 to 26, wherein in the three-dimensional configuration, the occlusion device has an open portion to provide access to the internal volume.

28. The occlusion device of any one of Embodiments 22 to 27, wherein the monolithic structure comprises a uniform thickness.

29. The occlusion device of any one of Embodiments 22 to 28, wherein a surface area of the first surface is at least 2× greater than the internal volume.

30. The occlusion device of Embodiment 29, wherein the surface area of the first surface is at least 3× greater than the internal volume.

31. The occlusion device of any one of Embodiments 22 to 30, wherein the monolithic structure comprises a reinforcing portion with no porosity.

32. The occlusion device of Embodiment 31, wherein the reinforcing portion extends around a periphery of the mesh structure.

33. The occlusion device of Embodiment 32, wherein the reinforcing portion extends around the entire periphery of the mesh structure.

34. The occlusion device of any one of Embodiments 22 to 33, wherein a first pore size of any pore in the first configuration is within 5 percent of a second pore size of the same pore in the second configuration.

35. The occlusion device of any one of Embodiments 22 to 34, wherein in the two-dimensional configuration, any pore size of the mesh structure is within 5 percent of the first mean pore size.

36. The occlusion device of any one of Embodiments 22 to 35, wherein in the three-dimensional configuration, any pore size of the mesh structure is within 5 percent of the second mean pore size.

37. The occlusion device of any one of Embodiments 22 to 36, wherein in the first configuration, the porosity has a uniform pore size.

38. The occlusion device of any one of Embodiments 22 to 37, wherein in the second configuration, the mesh structure is partially austenitic and partially martensitic.

39. The occlusion device of Embodiment 38, wherein the mesh structure is more austenitic than martensitic.

40. The occlusion device of any one of Embodiments 22 to 39, further comprising a volumetric filler disposed in the internal volume of the mesh structure.

41. The occlusion device of Embodiment 40, wherein the mesh structure comprises the volumetric filler.

42. A method of deploying an occlusion device, the method comprising:
releasing the occlusion device from a catheter and into an aneurysm sac, the occlusion device comprising:
a mesh structure having porosity, a first configuration in which the occlusion device is planar, and a second configuration in which the occlusion device is partially folded, wherein when the occlusion device is in the catheter, the occlusion device is in the second configuration; and transforming the occlusion device from the second configuration to a third configuration in which the occlusion device comprises an internal volume;

wherein a first pore size of any pore in the first configuration is within 5 percent of a second pore size of the same pore in the second configuration.

43. The method of Embodiment 42, further comprising filling the internal volume of the occlusion device with a volumetric filler.

44. The method of Embodiment 43, wherein filling the internal volume comprises folding a portion of the mesh structure into the internal volume of the occlusion device.

45. The method of any one of Embodiments 42 to 44, wherein in the first configuration, the mesh structure comprises a uniform pore size.

46. The method of any one of Embodiments 42 to 45, wherein in the third configuration, the occlusion device is at least partially spherical.

47. The method of any one of Embodiments 42 to 45, wherein in the third configuration, the occlusion device is at least partially cylindrical.

48. The method of any one of Embodiments 42 to 47, the mesh structure comprises a monolithic sheet.

What is claimed is:

1. An occlusion device comprising:
   a monolithic sheet comprising a mesh structure comprising a first surface and a second surface, at least a portion of the mesh structure comprises porosity, the mesh structure being configured to transition between a two-dimensional configuration and a three-dimensional configuration, the monolithic sheet further comprising a reinforcing portion with no porosity;
   wherein in the two-dimensional configuration and at rest, the first surface is parallel to the second surface and the mesh structure comprises a plurality of rounded segments connected end-to-end,
   wherein in the three-dimensional configuration, the occlusion device comprises an internal volume, and
   wherein the reinforcing portion extends around an outer edge of the mesh structure.

2. The occlusion device of claim 1, wherein the mesh structure comprises a thickness of no more than 0.002 inches.

3. The occlusion device of claim 1, wherein in the three-dimensional configuration, the occlusion device is at least partially spherical.

4. The occlusion device of claim 1, wherein in the three-dimensional configuration, the occlusion device is at least partially cylindrical.

5. The occlusion device of claim 1, wherein the mesh structure comprises a uniform thickness.

6. The occlusion device of claim 1, wherein the reinforcing portion extends around the entire outer edge of the mesh structure.

7. The occlusion device of claim 1, wherein in the three-dimensional configuration, the occlusion device has an open portion to provide access to the internal volume.

8. The occlusion device of claim 1, wherein in the two-dimensional configuration, the entire porosity has a uniform pore size.

9. The occlusion device of claim 1, wherein in the two-dimensional configuration, any pore size of the porosity is within 10 percent of a first mean pore size of the entire porosity of the two-dimensional configuration.

10. The occlusion device of claim 1, wherein in the three-dimensional configuration, any pore size of the mesh structure is within 10 percent of a second mean pore size of the entire porosity of the two-dimensional configuration.

11. The occlusion device of claim 1, wherein in the three-dimensional configuration, the mesh structure is partially austenitic and partially martensitic.

12. The occlusion device of claim 1, further comprising a volumetric filler disposed in the internal volume of the mesh structure.

13. The occlusion device of claim 1, wherein the reinforcing portion extends across a central axis of each of the plurality of rounded segments.

14. The occlusion device of claim 1, wherein each of the plurality of rounded segments has a length along a major axis and a width along a minor axis, the length being greater than the width.

15. The occlusion device of claim 1, wherein the monolithic sheet comprises a hole at a non-porous transition between adjacent rounded segments.

16. The occlusion device of claim 1, wherein in the three-dimensional configuration, adjacent longitudinal edges of the plurality of rounded segments overlap.

17. The occlusion device of claim 14, wherein the reinforcing portion further comprises a horizontal reinforcing portion extending across the major axis of each of the plurality of rounded segments.

18. The occlusion device of claim 17, wherein the reinforcing portion further comprises a vertical reinforcing portion extending across the minor axis of each of the plurality of rounded segments.

* * * * *